(12) United States Patent
Schaeffer et al.

(10) Patent No.: US 9,913,661 B2
(45) Date of Patent: Mar. 13, 2018

(54) MEDICAL DEVICES HAVING A RELEASABLE TUBULAR MEMBER AND METHODS OF USING THE SAME

(71) Applicant: Cook Medical Technologies LLC, Bloomington, IN (US)

(72) Inventors: Darin Schaeffer, Bloomington, IN (US); Kathryn Hardert, Bloomington, IN (US); Joshua Haines, West Chester, OH (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 396 days.

(21) Appl. No.: 14/816,198

(22) Filed: Aug. 3, 2015

(65) Prior Publication Data

US 2016/0030080 A1 Feb. 4, 2016

Related U.S. Application Data

(60) Provisional application No. 62/032,719, filed on Aug. 4, 2014.

(51) Int. Cl.
*A61B 17/34* (2006.01)
*A61B 17/00* (2006.01)

(52) U.S. Cl.
CPC .......... *A61B 17/34* (2013.01); *A61B 17/3415* (2013.01); *A61B 17/3421* (2013.01); *A61B 17/3423* (2013.01); *A61B 17/3417* (2013.01); *A61B 2017/00477* (2013.01); *A61B 2017/345* (2013.01); *A61B 2017/3492* (2013.01)

(58) Field of Classification Search
CPC . A61B 17/34; A61B 17/3401; A61B 17/3403; A61B 17/3415; A61B 17/3417; A61B 17/3421; A61B 17/3423; A61B 2017/3407; A61B 2017/3419;
(Continued)

(56) References Cited

U.S. PATENT DOCUMENTS 3,663,965 A 5/1972 Lee, Jr. et al.
3,818,511 A 6/1974 Goldberg et al.
(Continued)

FOREIGN PATENT DOCUMENTS

CN 1644155 7/2005
EP 0577400 1/1994
(Continued)

OTHER PUBLICATIONS

International Searching Authority, "IPER," for Int. App. No. PCT/US2014/049589, dated Feb. 18, 2016, pp. 1-13.
(Continued)

*Primary Examiner* — Eric S Gibson
(74) *Attorney, Agent, or Firm* — Buchanan Van Tuinen LLC

(57) ABSTRACT

Medical devices that have a releasable intermediate member and tubular member are described. Methods of using medical devices that have a releasable intermediate member and tubular member are also described. An example medical device comprises an elongate member, an intermediate member, and a tubular member. Each of the intermediate member and tubular member is releasably disposed on the elongate member.

20 Claims, 9 Drawing Sheets

(58) Field of Classification Search
CPC ...... A61B 2017/3454; A61B 2017/347; A61B 2017/348; A61B 2017/3492
USPC .................................................. 600/201–210
See application file for complete search history.

(56) References Cited

U.S. PATENT DOCUMENTS

| | | | |
|---|---|---|---|
| 4,024,859 A | 5/1977 | Slepyan et al. | |
| 4,064,873 A | 12/1977 | Swenson | |
| 4,217,664 A | 8/1980 | Faso | |
| 4,338,937 A | 7/1982 | Lerman | |
| 4,449,974 A | 5/1984 | Messingschlager | |
| 4,608,972 A | 9/1986 | Small | |
| 4,623,348 A | 11/1986 | Feit | |
| 4,753,656 A | 6/1988 | Tofield et al. | |
| 4,917,604 A | 4/1990 | Small | |
| 5,084,064 A | 1/1992 | Barak et al. | |
| 5,117,839 A | 6/1992 | Dance | |
| 5,176,649 A * | 1/1993 | Wakabayashi ..... | A61B 17/3431 604/164.09 |
| 5,304,142 A | 4/1994 | Liebl et al. | |
| 5,308,318 A | 5/1994 | Plassche, Jr. | |
| 5,389,088 A | 2/1995 | Hageman | |
| 5,425,761 A | 6/1995 | Lundgren | |
| 5,477,860 A | 12/1995 | Essen-Moller | |
| 5,489,278 A | 2/1996 | Abrahamson | |
| 5,674,191 A | 10/1997 | Edwards et al. | |
| 5,715,840 A | 2/1998 | Hall | |
| 5,782,807 A * | 7/1998 | Falvai ............... | A61M 25/0097 604/164.1 |
| 5,830,195 A | 11/1998 | Peters et al. | |
| 5,951,518 A | 9/1999 | Licata et al. | |
| 5,954,050 A | 9/1999 | Christopher | |
| 5,974,724 A | 9/1999 | Frantz et al. | |
| 5,988,171 A | 11/1999 | Sohn et al. | |
| 6,159,158 A | 12/2000 | Lowe | |
| 6,159,179 A | 12/2000 | Simonson | |
| 6,159,208 A | 12/2000 | Hovda et al. | |
| 6,397,841 B1 | 6/2002 | Kenyon et al. | |
| 6,408,851 B1 | 6/2002 | Karell | |
| 6,505,625 B1 | 1/2003 | Uenishi | |
| 6,513,530 B2 | 2/2003 | Knudson et al. | |
| 6,513,531 B2 | 2/2003 | Knudson et al. | |
| 6,523,541 B2 | 2/2003 | Knudson et al. | |
| 6,527,737 B2 | 3/2003 | Kaneshige | |
| 6,536,424 B2 | 3/2003 | Fitton | |
| 6,536,439 B1 | 3/2003 | Palmisano | |
| 6,585,703 B1 * | 7/2003 | Kassel ............... | A61M 25/0612 604/192 |
| 6,619,290 B1 | 9/2003 | Zacco | |
| 6,764,464 B2 | 7/2004 | McGuckin, Jr. et al. | |
| 6,895,963 B1 | 5/2005 | Martin et al. | |
| 6,910,483 B2 | 6/2005 | Daly et al. | |
| 6,955,172 B2 | 10/2005 | Nelson et al. | |
| 6,966,319 B2 | 11/2005 | Fitton | |
| 6,974,419 B1 | 12/2005 | Voss et al. | |
| 7,004,172 B1 | 2/2006 | Zacco | |
| 7,004,941 B2 | 2/2006 | Tvinnereim et al. | |
| 7,037,290 B2 | 5/2006 | Gardeski et al. | |
| 7,047,979 B2 | 5/2006 | Conrad et al. | |
| 7,063,089 B2 | 6/2006 | Knudson et al. | |
| 7,073,505 B2 | 7/2006 | Nelson et al. | |
| 7,090,672 B2 | 8/2006 | Underwood et al. | |
| 7,128,069 B2 | 10/2006 | Farrugia et al. | |
| 7,168,429 B2 | 1/2007 | Matthews et al. | |
| 7,188,627 B2 | 3/2007 | Nelson et al. | |
| 7,195,646 B2 | 3/2007 | Nahleili | |
| 7,213,599 B2 | 5/2007 | Conrad et al. | |
| 7,216,647 B2 | 5/2007 | Lang et al. | |
| 7,232,462 B2 | 6/2007 | Schaeffer | |
| 7,255,109 B2 | 8/2007 | Knudson et al. | |
| 7,269,453 B2 | 9/2007 | Mogul | |
| 7,291,112 B2 | 11/2007 | Martin et al. | |
| 7,337,778 B2 | 3/2008 | Martin et al. | |
| 7,337,781 B2 | 3/2008 | Vassallo | |
| 7,360,542 B2 | 4/2008 | Nelson et al. | |
| 7,363,926 B2 | 4/2008 | Pflueger et al. | |
| 7,387,634 B2 | 6/2008 | Benderev | |
| 7,401,611 B2 | 7/2008 | Conrad et al. | |
| 7,491,200 B2 | 2/2009 | Underwood | |
| 7,507,258 B2 | 3/2009 | Nahleili | |
| 7,607,439 B2 | 10/2009 | Li | |
| 7,644,714 B2 | 1/2010 | Atkinson et al. | |
| 7,658,192 B2 | 2/2010 | Harrington | |
| 7,669,603 B2 | 3/2010 | Knudson et al. | |
| 7,673,635 B2 | 3/2010 | Conrad et al. | |
| 7,680,538 B2 | 3/2010 | Durand et al. | |
| 7,703,460 B2 | 4/2010 | Conrad et al. | |
| 7,731,708 B2 | 6/2010 | Haarala et al. | |
| 7,762,991 B2 | 7/2010 | Bierman et al. | |
| 7,766,926 B2 | 8/2010 | Bosley, Jr. et al. | |
| 7,770,582 B2 | 8/2010 | Chen et al. | |
| 7,789,843 B2 | 9/2010 | Ray | |
| 7,793,661 B2 | 9/2010 | Macken | |
| 7,798,149 B2 | 9/2010 | Haduong | |
| 7,810,502 B1 | 10/2010 | Nguyen et al. | |
| 7,810,503 B2 | 10/2010 | Magnin | |
| 7,813,812 B2 | 10/2010 | Kieval et al. | |
| 7,819,122 B2 | 10/2010 | Abramson | |
| 7,827,038 B2 | 11/2010 | Richard et al. | |
| 7,827,988 B2 | 11/2010 | Matthews et al. | |
| 7,827,991 B2 | 11/2010 | Maher | |
| 7,832,402 B2 | 11/2010 | Nelissen | |
| 7,832,403 B2 | 11/2010 | Halstrom et al. | |
| 7,836,888 B2 | 11/2010 | Hegde et al. | |
| 7,836,889 B2 | 11/2010 | Kusukawa | |
| 7,845,356 B2 | 12/2010 | Paraschac et al. | |
| 7,845,357 B2 | 12/2010 | Buscemi et al. | |
| 7,856,979 B2 | 12/2010 | Doshi et al. | |
| 7,856,980 B2 | 12/2010 | Lang et al. | |
| 7,861,722 B2 | 1/2011 | Keropian | |
| 7,861,723 B2 | 1/2011 | Dedrick et al. | |
| 7,861,724 B2 | 1/2011 | Keropian | |
| 7,862,721 B2 | 1/2011 | Bergersen | |
| 7,870,860 B2 | 1/2011 | McCormick et al. | |
| 7,874,291 B2 | 1/2011 | Ging et al. | |
| 7,874,294 B2 | 1/2011 | Burger | |
| 7,884,101 B2 | 2/2011 | Teegarden et al. | |
| 7,909,037 B2 | 3/2011 | Hegde et al. | |
| 7,909,038 B2 | 3/2011 | Hegde et al. | |
| 7,918,228 B2 | 4/2011 | Smernoff | |
| 7,921,850 B2 | 4/2011 | Nelson et al. | |
| 7,934,506 B2 | 5/2011 | Woodson et al. | |
| 7,935,065 B2 | 5/2011 | Martin et al. | |
| 7,938,114 B2 | 5/2011 | Matthews et al. | |
| 7,949,400 B2 | 5/2011 | Kieval et al. | |
| 7,954,494 B1 | 6/2011 | Connor | |
| 7,954,496 B2 | 6/2011 | Jansheski et al. | |
| 7,955,267 B2 | 6/2011 | Voss et al. | |
| 7,958,895 B2 | 6/2011 | Nelson et al. | |
| 7,958,896 B2 | 6/2011 | Nelson et al. | |
| 7,959,554 B2 | 6/2011 | McAlexander et al. | |
| 7,971,591 B2 | 7/2011 | Jansheski | |
| 7,975,700 B2 | 7/2011 | Frazier et al. | |
| 7,975,701 B2 | 7/2011 | Bergersen | |
| 7,976,471 B2 | 7/2011 | Martin et al. | |
| 7,980,248 B2 | 7/2011 | Hegde et al. | |
| 7,984,714 B2 | 7/2011 | Hausmann et al. | |
| 7,987,854 B2 | 8/2011 | Arni | |
| 7,992,564 B2 | 8/2011 | Doshi | |
| 7,992,566 B2 | 8/2011 | Pflueger et al. | |
| 7,992,567 B2 | 8/2011 | Hirotsuka et al. | |
| 7,997,266 B2 | 8/2011 | Frazier et al. | |
| 7,997,267 B2 | 8/2011 | Ging et al. | |
| 7,997,276 B2 | 8/2011 | Goff | |
| 8,001,971 B2 | 8/2011 | Boucher et al. | |
| 8,001,972 B2 | 8/2011 | Eubank | |
| 8,001,973 B2 | 8/2011 | Solos et al. | |
| 8,015,975 B2 | 9/2011 | Zohlmann, Jr. | |
| 8,020,560 B2 | 9/2011 | Paraschac et al. | |
| 8,025,063 B2 | 9/2011 | Sotos et al. | |
| 8,026,405 B2 | 9/2011 | Beaudry | |
| 8,028,703 B1 | 10/2011 | Moses | |
| 8,033,282 B2 | 10/2011 | Eubank | |

(56) References Cited

U.S. PATENT DOCUMENTS

| | | |
|---|---|---|
| 8,037,885 B2 | 10/2011 | Metzger et al. |
| 8,037,886 B2 | 10/2011 | Solos et al. |
| 8,047,201 B2 | 11/2011 | Guyuron et al. |
| 8,047,206 B2 | 11/2011 | Boucher et al. |
| 8,052,646 B2 * | 11/2011 | Schweikert ....... A61M 25/0097 604/167.04 |
| 8,070,693 B2 | 12/2011 | Ayala et al. |
| 8,074,655 B2 | 12/2011 | Sanders |
| 8,096,303 B2 | 1/2012 | Dineen et al. |
| 8,147,456 B2 | 4/2012 | Fisher et al. |
| 8,167,787 B2 | 5/2012 | Gillis |
| 8,220,466 B2 | 7/2012 | Frazier et al. |
| 8,220,467 B2 | 7/2012 | Sanders |
| 8,327,854 B2 | 12/2012 | Gillis et al. |
| 8,414,537 B2 | 4/2013 | Nardeo et al. |
| 8,425,466 B2 | 4/2013 | Sargent, Jr. |
| 8,460,322 B2 | 6/2013 | van der Burg et al. |
| 8,529,544 B2 | 9/2013 | Haarala et al. |
| 8,535,310 B2 | 9/2013 | Hardin, Jr. et al. |
| 8,535,349 B2 | 9/2013 | Chen et al. |
| 8,603,185 B2 | 12/2013 | Shah et al. |
| 2001/0050085 A1 | 12/2001 | Knudson et al. |
| 2003/0111079 A1 | 6/2003 | Matthews et al. |
| 2003/0140925 A1 | 7/2003 | Sapienza et al. |
| 2003/0168064 A1 | 9/2003 | Daly et al. |
| 2004/0028676 A1 | 2/2004 | Klein et al. |
| 2004/0073272 A1 | 4/2004 | Knudson et al. |
| 2004/0099275 A1 | 5/2004 | Zacco |
| 2004/0112387 A1 | 6/2004 | Lang et al. |
| 2004/0153127 A1 | 8/2004 | Gordon et al. |
| 2004/0187870 A1 | 9/2004 | Matthews et al. |
| 2005/0005937 A1 | 1/2005 | Farrugia et al. |
| 2005/0098184 A1 | 5/2005 | Conrad et al. |
| 2005/0103339 A1 | 5/2005 | Daly et al. |
| 2005/0126563 A1 | 6/2005 | van der Burg et al. |
| 2005/0217673 A1 | 10/2005 | Daly et al. |
| 2005/0256452 A1 | 11/2005 | DeMarchi et al. |
| 2005/0267547 A1 | 12/2005 | Knudson et al. |
| 2005/0268914 A1 | 12/2005 | Paoluccio et al. |
| 2005/0279365 A1 | 12/2005 | Armijo et al. |
| 2006/0000475 A1 | 1/2006 | Matthews et al. |
| 2006/0070626 A1 | 4/2006 | Frazier et al. |
| 2006/0112962 A1 | 6/2006 | Tebbutt et al. |
| 2006/0150986 A1 | 7/2006 | Roue et al. |
| 2006/0169289 A1 | 8/2006 | Zacco |
| 2006/0201519 A1 | 9/2006 | Frazier et al. |
| 2006/0201520 A1 | 9/2006 | Christensen, III |
| 2006/0207606 A1 | 9/2006 | Roue et al. |
| 2006/0207607 A1 | 9/2006 | Hirotsuka et al. |
| 2006/0207608 A1 | 9/2006 | Hirotsuka et al. |
| 2006/0207612 A1 | 9/2006 | Jackson et al. |
| 2006/0235264 A1 | 10/2006 | Vassallo |
| 2006/0235877 A1 | 10/2006 | Richard et al. |
| 2006/0263145 A1 | 11/2006 | Pal et al. |
| 2007/0016166 A1 | 1/2007 | Thistle |
| 2007/0132117 A1 | 6/2007 | Truitt et al. |
| 2007/0134085 A1 | 6/2007 | Daly et al. |
| 2007/0144539 A1 | 6/2007 | van der Burg et al. |
| 2007/0157928 A1 | 7/2007 | Pujol et al. |
| 2007/0157934 A1 | 7/2007 | Lang et al. |
| 2007/0207994 A1 | 9/2007 | Teegarden et al. |
| 2007/0209664 A1 | 9/2007 | Paraschac et al. |
| 2007/0209665 A1 | 9/2007 | Gillis et al. |
| 2007/0244086 A1 | 10/2007 | Teegarden et al. |
| 2007/0256693 A1 | 11/2007 | Paraschac et al. |
| 2007/0287923 A1 | 12/2007 | Adkins et al. |
| 2008/0023012 A1 | 1/2008 | Dineen et al. |
| 2008/0027480 A1 | 1/2008 | van der Burg et al. |
| 2008/0027560 A1 | 1/2008 | Jackson et al. |
| 2008/0035160 A1 | 2/2008 | Woodson et al. |
| 2008/0041382 A1 | 2/2008 | Matthews et al. |
| 2008/0041383 A1 | 2/2008 | Matthews et al. |
| 2008/0041398 A1 | 2/2008 | Hegde et al. |
| 2008/0045813 A1 | 2/2008 | Phuah et al. |
| 2008/0053461 A1 | 3/2008 | Hirotsuka et al. |
| 2008/0058584 A1 | 3/2008 | Hirotsuka et al. |
| 2008/0066753 A1 | 3/2008 | Martin et al. |
| 2008/0066765 A1 | 3/2008 | Paraschac et al. |
| 2008/0066769 A1 | 3/2008 | Dineen et al. |
| 2008/0097380 A1 | 4/2008 | Li |
| 2008/0099019 A1 | 5/2008 | Martin et al. |
| 2008/0115791 A1 | 5/2008 | Heine |
| 2008/0194953 A1 | 8/2008 | Kerber |
| 2008/0208265 A1 | 8/2008 | Frazier et al. |
| 2008/0251071 A1 | 10/2008 | Armitstead et al. |
| 2008/0306442 A1 * | 12/2008 | Bardsley ............ A61B 17/3421 604/104 |
| 2009/0044814 A1 | 2/2009 | Iancea et al. |
| 2009/0053306 A1 | 2/2009 | Agarwal et al. |
| 2009/0060905 A1 | 3/2009 | Martin et al. |
| 2009/0088599 A1 | 4/2009 | Zook et al. |
| 2009/0099471 A1 | 4/2009 | Broadley et al. |
| 2009/0131923 A1 | 5/2009 | Connors et al. |
| 2010/0004264 A1 | 1/2010 | Xiang et al. |
| 2010/0010061 A1 | 1/2010 | Cooper et al. |
| 2010/0016694 A1 | 1/2010 | Martin et al. |
| 2010/0028026 A1 | 2/2010 | Inami et al. |
| 2010/0106246 A1 | 4/2010 | Rousseau et al. |
| 2010/0108066 A1 | 5/2010 | Martin et al. |
| 2010/0108077 A1 | 5/2010 | Lindh et al. |
| 2010/0132719 A1 | 6/2010 | Jacobs et al. |
| 2010/0144701 A1 | 6/2010 | Cooper et al. |
| 2010/0234946 A1 | 9/2010 | Rousseau |
| 2010/0286793 A1 | 11/2010 | Newman et al. |
| 2010/0300458 A1 | 12/2010 | Stubbs et al. |
| 2011/0005526 A1 | 1/2011 | Garabadian et al. |
| 2011/0005529 A1 | 1/2011 | Doshi et al. |
| 2011/0005530 A1 | 1/2011 | Doshi et al. |
| 2011/0017220 A1 | 1/2011 | Lindsay et al. |
| 2011/0030700 A1 | 2/2011 | Wilson |
| 2011/0030701 A1 | 2/2011 | Lang et al. |
| 2011/0036357 A1 | 2/2011 | Abramson |
| 2011/0046712 A1 | 2/2011 | Melsheimer et al. |
| 2011/0048430 A1 | 3/2011 | Arnon |
| 2011/0048431 A1 | 3/2011 | Li |
| 2011/0056498 A1 | 3/2011 | Lang et al. |
| 2011/0067708 A1 | 3/2011 | Doshi et al. |
| 2011/0067709 A1 | 3/2011 | Doshi et al. |
| 2011/0073119 A1 | 3/2011 | Chen et al. |
| 2011/0088701 A1 | 4/2011 | Thornton |
| 2011/0092910 A1 | 4/2011 | Schultz |
| 2011/0094520 A1 | 4/2011 | Mikhailenok et al. |
| 2011/0100376 A1 | 5/2011 | Rousseau |
| 2011/0100378 A1 | 5/2011 | Rousseau |
| 2011/0108041 A1 | 5/2011 | Sather et al. |
| 2011/0114099 A1 | 5/2011 | Goldstein |
| 2011/0120476 A1 | 5/2011 | Keropian |
| 2011/0130249 A1 | 6/2011 | Mikhailenok et al. |
| 2011/0132378 A1 | 6/2011 | Levendowski et al. |
| 2011/0155142 A1 | 6/2011 | Boucher et al. |
| 2011/0155143 A1 | 6/2011 | Shantha |
| 2011/0155144 A1 | 6/2011 | Toussaint |
| 2011/0162658 A1 | 7/2011 | Fisher et al. |
| 2011/0166673 A1 | 7/2011 | Patel et al. |
| 2011/0168186 A1 | 7/2011 | Halstrom |
| 2011/0168187 A1 | 7/2011 | Nelissen |
| 2011/0168188 A1 | 7/2011 | Moore et al. |
| 2011/0174315 A1 | 7/2011 | Zhang et al. |
| 2011/0178439 A1 | 7/2011 | Irwin et al. |
| 2011/0180075 A1 | 7/2011 | Chen et al. |
| 2011/0180076 A1 | 7/2011 | Hegde et al. |
| 2011/0183928 A1 | 7/2011 | Thede et al. |
| 2011/0192404 A1 | 8/2011 | Chen |
| 2011/0203598 A1 | 8/2011 | Favet et al. |
| 2011/0214678 A1 | 9/2011 | Zhang et al. |
| 2011/0218451 A1 | 9/2011 | Lai et al. |
| 2011/0220123 A1 | 9/2011 | Robson |
| 2011/0220124 A1 | 9/2011 | Vaska et al. |
| 2011/0220125 A1 | 9/2011 | Van Dyke et al. |
| 2011/0224678 A1 * | 9/2011 | Gabbay ............ A61B 17/3468 606/108 |
| 2011/0226261 A1 | 9/2011 | Hernandez |
| 2011/0226262 A1 | 9/2011 | Gillis et al. |
| 2011/0226263 A1 | 9/2011 | Gillis et al. |

(56) References Cited

U.S. PATENT DOCUMENTS

| | | | |
|---|---|---|---|
| 2011/0226264 A1 | 9/2011 | Friedman et al. | |
| 2011/0232651 A1 | 9/2011 | Diers | |
| 2011/0232652 A1 | 9/2011 | Levendowski et al. | |
| 2011/0240037 A1 | 10/2011 | Hegde et al. | |
| 2011/0240038 A1 | 10/2011 | Doshi et al. | |
| 2011/0245850 A1 | 10/2011 | van der Burg et al. | |
| 2011/0259345 A1 | 10/2011 | Cullen | |
| 2011/0259346 A1 | 10/2011 | Tsuiki et al. | |
| 2011/0265801 A1 | 11/2011 | Cullen | |
| 2011/0265802 A1 | 11/2011 | Ha | |
| 2011/0308530 A1 | 12/2011 | Gillis et al. | |
| 2012/0041271 A1* | 2/2012 | Wenchell | A61B 17/3439 600/208 |
| 2012/0162401 A1 | 6/2012 | Melder et al. | |
| 2012/0226341 A1* | 9/2012 | Schreck | A61F 2/966 623/1.12 |
| 2012/0265055 A1 | 10/2012 | Melsheimer et al. | |
| 2013/0041314 A1 | 2/2013 | Dillon | |
| 2013/0046138 A1 | 2/2013 | McLawhorn | |
| 2013/0056009 A1 | 3/2013 | Mohan et al. | |
| 2013/0060267 A1 | 3/2013 | Farnan et al. | |
| 2013/0085546 A1 | 4/2013 | Bolea et al. | |
| 2013/0123705 A1 | 5/2013 | Holm et al. | |
| 2013/0180528 A1 | 7/2013 | Zhou et al. | |
| 2013/0213409 A1 | 8/2013 | Podmore et al. | |
| 2013/0226146 A1 | 8/2013 | Tekulve | |
| 2013/0237967 A1 | 9/2013 | Schaeffer et al. | |
| 2013/0237968 A1 | 9/2013 | Schaeffer et al. | |
| 2013/0238003 A1 | 9/2013 | Fischer et al. | |
| 2013/0245662 A1 | 9/2013 | Schaeffer et al. | |
| 2014/0102460 A1 | 4/2014 | Catalano | |
| 2016/0007984 A1* | 1/2016 | Schaeffer | A61B 17/34 600/210 |
| 2016/0030080 A1* | 2/2016 | Schaeffer | A61B 17/3423 600/204 |

FOREIGN PATENT DOCUMENTS

| | | |
|---|---|---|
| EP | 1159924 | 12/2001 |
| EP | 1501447 | 3/2009 |
| WO | 199734649 | 9/1997 |
| WO | WO9734649 | 9/1997 |
| WO | WO199734649 | 9/1997 |
| WO | WO199850093 | 11/1998 |
| WO | WO2003075794 | 9/2003 |
| WO | WO2005056079 | 6/2005 |
| WO | WO2005058409 | 6/2005 |
| WO | WO2007056583 | 5/2007 |
| WO | WO2007149469 | 12/2007 |
| WO | WO2009140197 | 11/2009 |
| WO | WO2010045546 | 4/2010 |
| WO | WO2010051195 | 5/2010 |
| WO | WO2011068952 | 6/2011 |
| WO | WO2011123714 | 10/2011 |
| WO | WO2013010169 | 1/2013 |
| WO | WO2015020953 | 9/2013 |
| WO | 2013158906 | 10/2013 |
| WO | WO2013158906 | 10/2013 |
| WO | WO2014189540 | 11/2014 |
| WO | WO2015020953 | 2/2015 |

OTHER PUBLICATIONS

The International Bureau of WIPO, International Preliminary Report on Patentability, dated Feb. 7, 2017, p. 1-8.
File history of U.S. Appl. No. 08/883,220, now U.S. Pat. No. 5,988,171, as of Jun. 3, 2014, filed Jun. 26, 1997. First Named Inventor, Ze'ev Sohn. Title, Methods and Devices for the Treatment of Airway Obstruction, Sleep Apnea and Snoring.
File history of U.S. Appl. No. 10/877,003, now U.S. Pat. No. 7,213,599, as of Jun. 3, 2014, filed Jun. 24, 2004. First Named Inventor, Timothy R. Conrad. Title, Airway Implant.
File history of U.S. Appl. No. 11/757,501, now U.S. Pat. No. 7,703,460, as of Jun. 3, 2014, filed Jun. 4, 2007. First Named Inventor, Timothy R. Conrad. Title, Tongue Implant.
File history of U.S. Appl. No. 12/214,084 as of Jun. 3, 2014, filed Jun. 17, 2008. First Named Inventor, Octavian Iancea. Title, Implantable devices, systems, and methods for maintaining desired orientations in targeted tissue regions.
Woodson et al,"Multicenter study of a novel adjustable tongue-advancement device for obstructive sleep apnea," Otolaryngology and Head and Neck Surgery, Jun. 10, 2010, pp. 585-590, 143(4), Sage Publications.
Woodson et al, "Response to: Multicenter study of a novel adjustable tongue-advancement device for obstructive sleep apnea," Otolaryngology and Head and Neck Surgery, 211, pp. 1009-1010, 144(6), Sage Publications.
Hamans et al, "A novel tongue implant for tongue advancement for obstructive sleep apnea: Feasibility, safety and histology in a canine model," Journal of Musculoskeletal and Neuronal Interactions, Dec. 29, 2009, pp. 100-111, 10(1), Hylonome.
Kezirian, Eric J., M.D.,M.P.H., "Drug-Induced Sleepy Endoscopy," Dr. Kezirian's Blog, pp. 1-3, http://www.sleep-doctor.com/surgical-treatment-overview/drug-induced-sleep-endoscopy/, 2009-2014.
Medical News Today, "Aspire Medical Announces First Implant in US and Start of Clinical Trial to Treat Sleep Apnea," www.medicalnewstoday.com, May 23, 2007.
Park, Dr. Steven Y., "Aspire Medical Advance System for obstructive sleep apnea," Dr. Park: Breathe better, sleep better, live better. pp. 1-4. Oct. 6, 2010. <http://doctorstevenpark.com/aspire-medical-advance-system-for-obstructive-sleep-apnea>.
PR Newswire, "Aspire Medical appoints Roseanne Varner as president and CEO [press release]," pp. 1-2. May 1, 2011. <http://www.prnewswire.com/news-releases/aspire-medical-appoints-roseanne-varner-as-president-and-ceo-57760852.html>.
Siesta Medical, "Siesta Medical Receives 510(k) Clearance for Encore System to treat Obstructive Sleep Apnea," Siesta Medical, Los Gatos, CA, Sep. 12, 2011.
Revent Medical, "The Revent Solution: Tongue Implanter Kit," 2014. pp. 1-2, Retrieved Aug. 12, 2014. <http://www.reventmedical.com/solution/>.
Revent Medical, "The Revent Solution: Implant," 2014. pp. 1-2, Retrieved Aug. 12, 2014. <www.reventmedical.com/solution/>.
Knobbe, Martens, Olson & Bear, LLP, "Amendment and response to non-Final Office Action dated Jan. 18, 2013, for U.S. Appl. No. 13/077,813," Mar. 31, 2011, First Named Inventor, van der Burg. Title, Suture Passer Systems and Methods for Tongue or Other Tissue Suspension and Compression.
Synmed, "E.G. Scan: Trans-nasal, disposable system for upper GI screening," SynMed Ltd., p. 1, United Kingdom.
Mizayahi, Soichiro, M.D., et al., "A trial study of RhinoSleep for the diagnosis of sleep apnea," Psychiatry and Clinical Neuroscience, 55, pp. 249-250, 2001.
International Searching Authority, International Search Report and Written Opinion for International application No. PCT/US2014/049341, dated Nov. 19, 2014, pp. 1-11.
Bosmed, "Laryngeal and Esophageal Products," Bosmed.com, accessed Oct. 1, 2012, p. 1.
Hood Laboratories, "Schaitkin Salivary Duct Cannula," HoodLabs.com, accessed Jan. 19, 2014, pp. 1-2.
Nahlieli, Oded, et. al., "Diagnosis and treatment of strictures and kinks in salivary gland ducts," J. Oral and Maxillofacial Surgery, vol. 59, Issue 5, pp. 484-490, May 2001.
International Searching Authority, International Search Report and Written Opinion for International application No. PCT/US2014/049589, dated Dec. 3, 2014, pp. 1-16.
International Searching Authority, International Search Report and Written Opinion for International application No. PCT/US2015/032577, dated Aug. 5, 2015, pp. 1-10.
International Searching Authority, "International Search Report and Written Opinion," for Int. App. No. PCT/US2015/043375, dated Oct. 8, 2015, pp. 1-12.

* cited by examiner

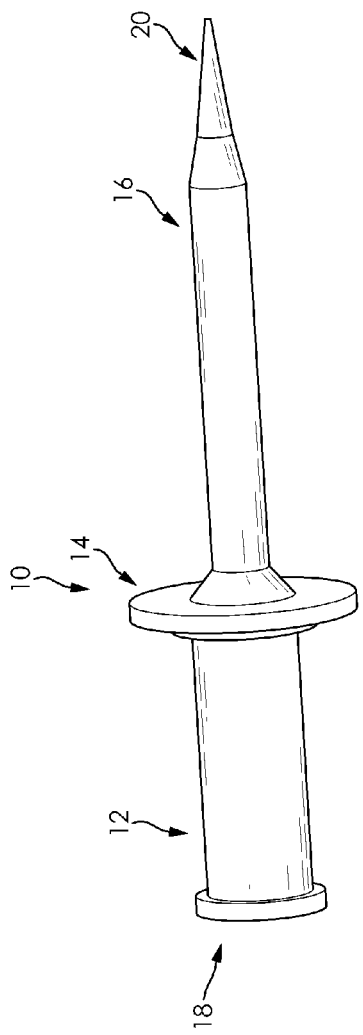
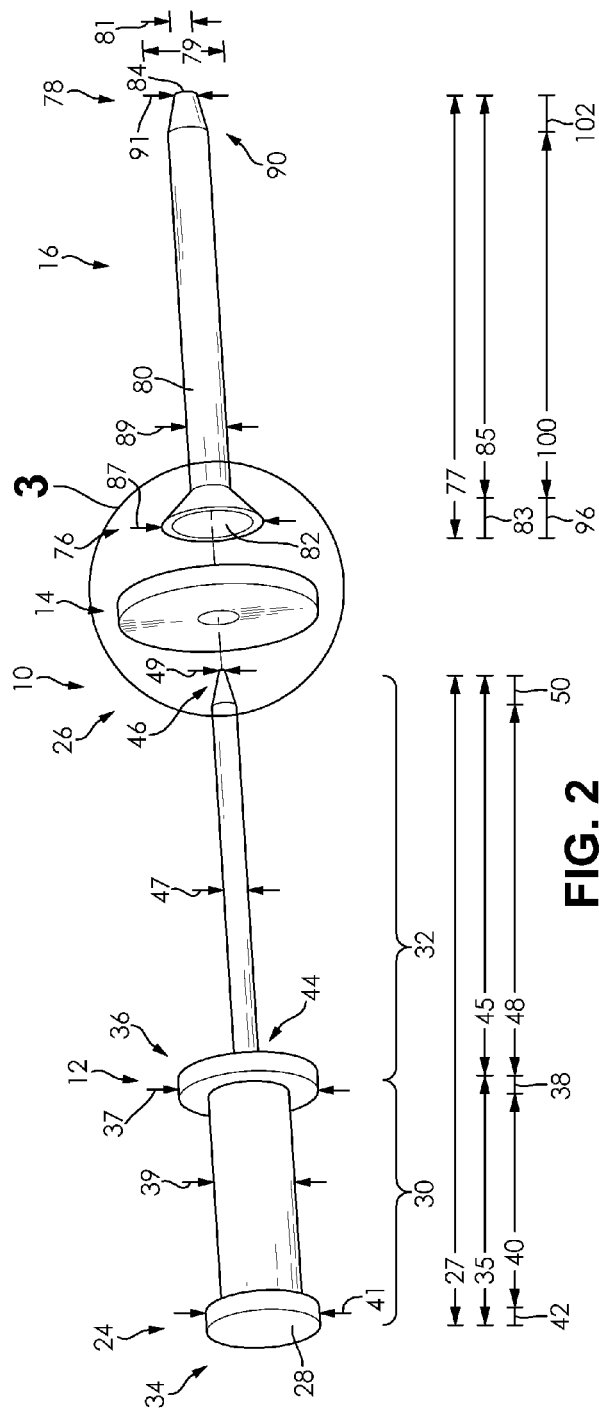

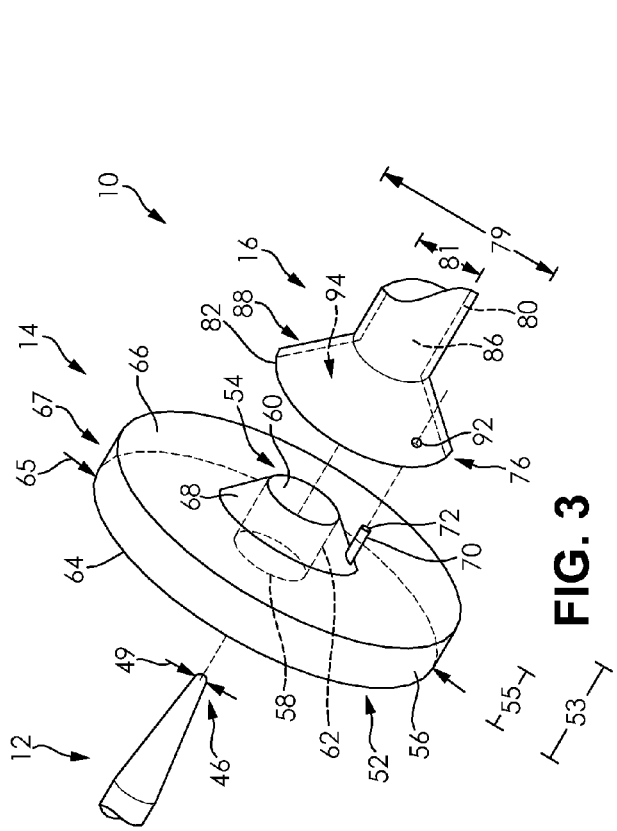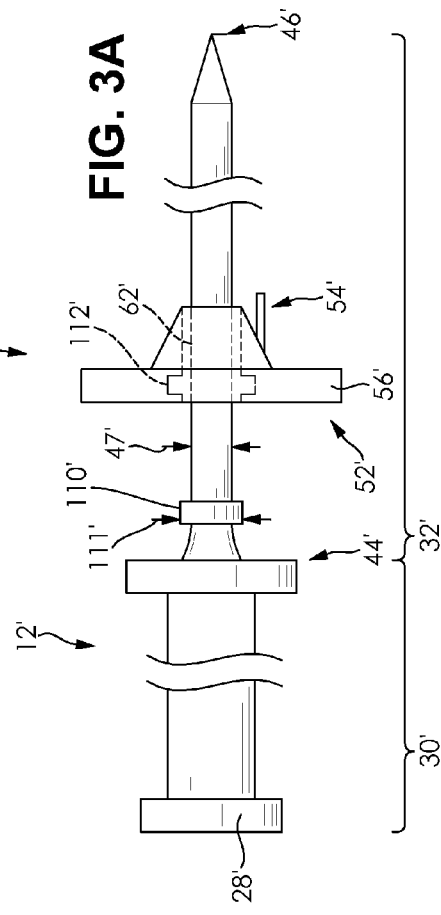

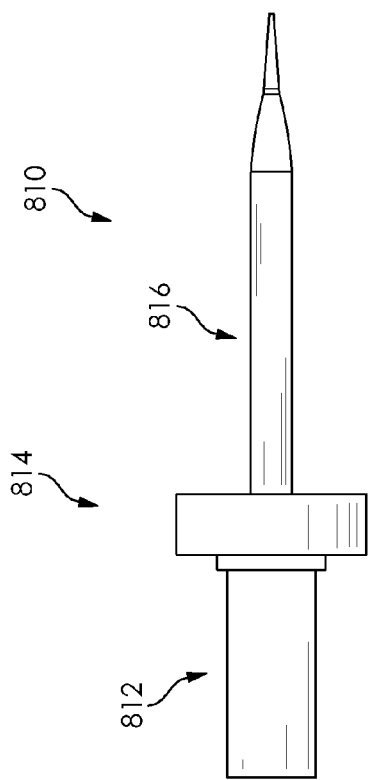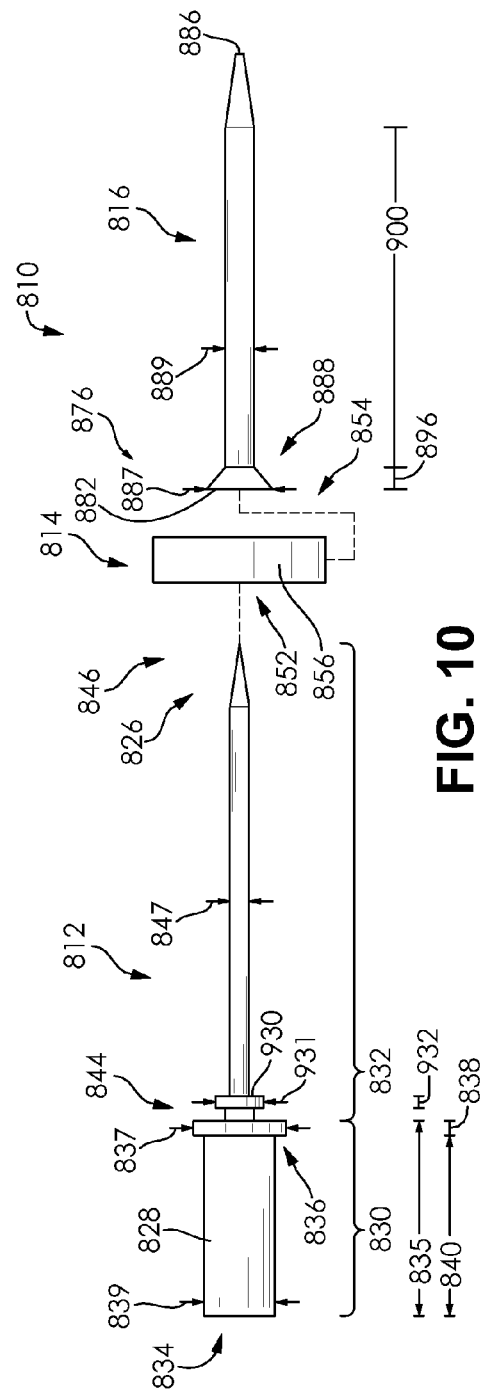

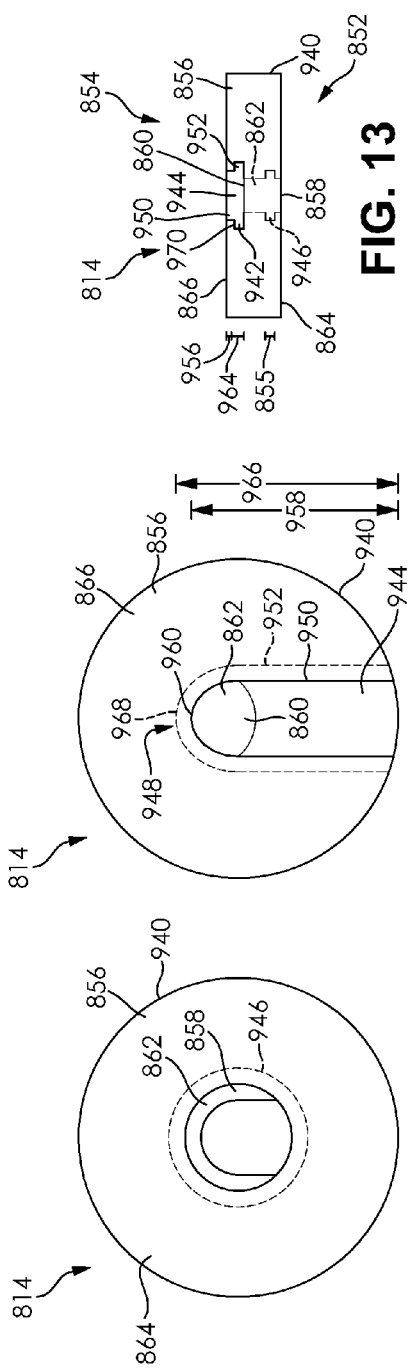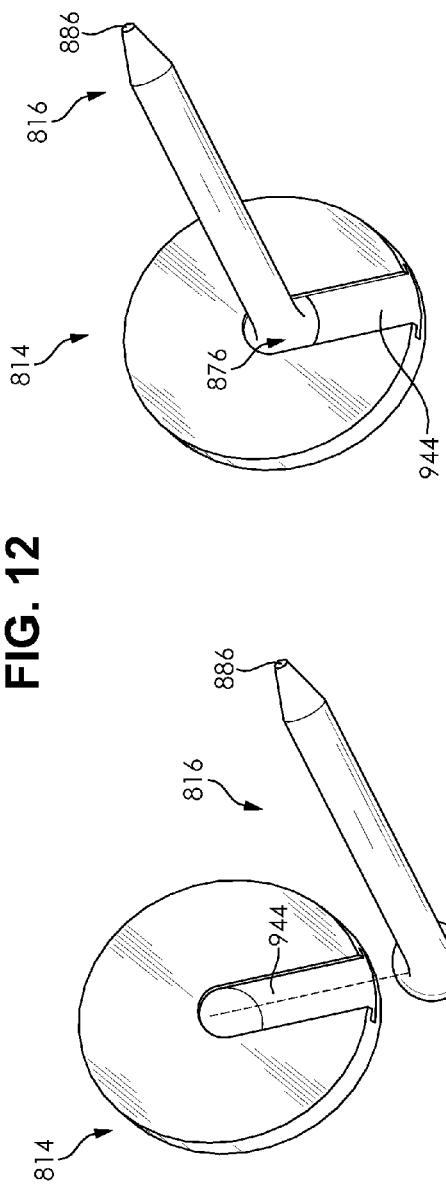

MEDICAL DEVICES HAVING A RELEASABLE TUBULAR MEMBER AND METHODS OF USING THE SAME

RELATED APPLICATION

This application claims the benefit of U.S. Provisional Application No. 62/032,719, filed Aug. 4, 2014. The entire disclosure of this related application is hereby incorporated into this disclosure by reference.

FIELD

The disclosure relates generally to the field of medical devices. Particular embodiments are related to medical devices that have a releasable tubular member and methods of using a medical device that has a releasable tubular member.

BACKGROUND

A variety of medical devices have been developed to treat bodily passages, such as the salivary glands. For example, some medical devices have been developed that can be introduced into a bodily passage to provide access to the bodily passage during the performance of a procedure. These devices, however, can be difficult to manipulate and position within the bodily passage and are often introduced and removed a number of times during treatment so that other procedures can be performed. The repeated introduction and removal of devices from the bodily passage during treatment increases patient discomfort and the likelihood of trauma. Therefore, a need exists for improved medical devices that can be introduced into a bodily passage and that can be used to provide access during treatment.

BRIEF SUMMARY OF SELECTED EXAMPLE EMBODIMENTS

A first example embodiment of a medical device comprises an elongate member, an intermediate member, and a tubular member. The elongate member has a proximal portion and a shaft that extends distally from the proximal portion. The proximal portion has a first proximal end, a first distal end, and a first outside diameter. The shaft has a second proximal end attached to the first distal end of the proximal portion, a second distal end, and a second outside diameter that is less than the first outside diameter. The intermediate member is releasably attached to the elongate member and is disposed on the shaft. The intermediate member has a third proximal end, a third distal end, a first surface, a second surface, an intermediate member body, and a third outside diameter that is greater than the first outside diameter of the proximal portion of the elongate member. The intermediate member body defines a first intermediate member opening, a second intermediate member opening, an intermediate member lumen, an edge, and a slot. The first intermediate member opening is defined on the first surface of the intermediate member. The second intermediate member opening is defined between the first surface and the second surface and is in communication with the slot. The intermediate member lumen extends from the first intermediate member opening to the second intermediate member opening. The intermediate member lumen has a first inside diameter that is less than the first outside diameter of the proximal portion of the elongate member. The edge extends from the first surface to the second surface of the intermediate member. The slot is cooperatively defined by the edge and the second surface and extends from the second surface into the intermediate member body. The tubular member is partially disposed within the slot defined by the intermediate member such that the tubular member is releasably attached to the intermediate member. The tubular member is disposed on the shaft of the elongate member and has a fourth proximal end, a fourth distal end, and a tubular member body. The tubular member body defines a first tubular member opening on the fourth proximal end, a second tubular member opening on the fourth distal end, and a tubular member lumen that extends from the first tubular member opening to the second tubular member opening.

A second example embodiment of a medical device comprises an elongate member, an intermediate member, and a tubular member. The elongate member has a proximal portion and a shaft that extends distally from the proximal portion. The proximal portion has a first proximal end, a first distal end, and a first outside diameter. The shaft has a second proximal end attached to the first distal end of the proximal portion, a second distal end, and a second outside diameter that is less than the first outside diameter. The intermediate member is releasably attached to the elongate member and is disposed on the shaft. The intermediate member has a third proximal end, a third distal end, a first surface, a second surface, an intermediate member body, and a third outside diameter that is greater than the first outside diameter of the proximal portion of the elongate member. The intermediate member body defines a first intermediate member opening, a second intermediate member opening, an intermediate member lumen, an edge, and a slot. The first intermediate member opening is defined on the first surface of the intermediate member. The second intermediate member opening is defined between the first surface and the second surface and is in communication with the slot. The intermediate member lumen extends from the first intermediate member opening to the second intermediate member opening. The intermediate member lumen has a first inside diameter that is less than the first outside diameter of the proximal portion of the elongate member. The edge extends from the first surface to the second surface of the intermediate member. The slot is cooperatively defined by the edge and the second surface and extends from the second surface into the intermediate member body. The slot has a first portion and a second portion. The first portion extends from the second surface toward the first surface and has a first width. The second portion extends from the first portion toward the first surface and has a second width that is greater than the first width. The tubular member is partially disposed within the slot defined by the intermediate member such that the tubular member is releasably attached to the intermediate member. The tubular member is disposed on the shaft of the elongate member and has a fourth proximal end, a fourth distal end, and a tubular member body. The tubular member body defines a first tubular member opening on the fourth proximal end, a second tubular member opening on the fourth distal end, a tubular member lumen that extends from the first tubular member opening to the second tubular member opening, a proximal portion that extends from the fourth proximal end toward the fourth distal end, and a distal portion that extends from the fourth distal end toward the fourth proximal end. The proximal portion of the tubular member has a fourth outside diameter that is greater than the first width of the slot. The distal portion of the tubular member has a fifth outside diameter that is less than the fourth outside diameter. The proximal portion of the tubular member is disposed within the slot defined by the intermediate member. The intermediate member lumen is in communication with the tubular member lumen.

A third example embodiment of a medical device comprises an elongate member, an intermediate member, and a tubular member. The elongate member has a proximal portion and a shaft that extends distally from the proximal portion. The proximal portion has a first proximal end, a first distal end, and a first outside diameter. The shaft has a second proximal end attached to the first distal end of the proximal portion, a tapered second distal end, a second outside diameter that is less than the first outside diameter, and a protuberance disposed between the second proximal end and the second distal end. The protuberance has a third outside diameter that is greater than the second outside diameter of the shaft. The intermediate member is releasably attached to the elongate member and is disposed on the shaft. The intermediate member has a third proximal end, a third distal end, a first surface, a second surface, an intermediate member body, and a fourth outside diameter that is greater than the first outside diameter of the proximal portion of the elongate member. The intermediate member body defines a first intermediate member opening, a second intermediate member opening, an intermediate member lumen, an edge, a slot, and a recess. The first intermediate member opening is defined on the first surface of the intermediate member. The second intermediate member opening is defined between the first surface and the second surface and is in communication with the slot. The intermediate member lumen extends from the first intermediate member opening to the second intermediate member opening. The intermediate member lumen has a first inside diameter that is less than the first outside diameter of the proximal portion of the elongate member. The edge extends from the first surface to the second surface of the intermediate member. The slot is cooperatively defined by the edge and the second surface and extends from the second surface into the intermediate member body. The slot has a first portion and a second portion. The first portion extends from the second surface toward the first surface and has a first width. The second portion extends from the first portion toward the first surface and has a second width that is greater than the first width. The recess is defined between the first intermediate member opening and the second intermediate member opening within the intermediate member lumen and has a second inside diameter that is greater than the first inside diameter of the intermediate member lumen. The tubular member is partially disposed within the slot defined by the intermediate member such that the tubular member is releasably attached to the intermediate member. The tubular member is disposed on the shaft of the elongate member and has a fourth proximal end, a tapered fourth distal end, and a tubular member body. The tubular member body defines a first tubular member opening on the fourth proximal end, a second tubular member opening on the fourth distal end, a tubular member lumen that extends from the first tubular member opening to the second tubular member opening, a frustoconical proximal portion that extends from the fourth proximal end and tapers toward the fourth distal end, and a distal portion that extends from the fourth distal end toward the fourth proximal end. The frustoconical proximal portion of the tubular member has a fifth outside diameter that is greater than the first width of the slot. The distal portion of the tubular member has a sixth outside diameter that is less than the fifth outside diameter. The frustoconical proximal portion of the tubular member is disposed within the slot defined by the intermediate member. The intermediate member lumen is in communication with the tubular member lumen. The protuberance of the shaft is disposed within the recess defined by the intermediate member. The fourth distal end of the tubular member is disposed between the second proximal end and the second distal end of the shaft.

BRIEF DESCRIPTION OF THE DRAWINGS

FIG. 1 is a perspective view of an embodiment of a medical device.

FIG. 2 is an exploded perspective view of the medical device illustrated in FIG. 1.

FIG. 3 is a magnified view of area 3 illustrated in FIG. 2.

FIG. 3A is a side view of another embodiment of an elongate member and an alternative intermediate member.

FIG. 9 is a side view of another embodiment of a medical device.

FIG. 10 is an exploded side view of the medical device illustrated in FIG. 9.

FIG. 11 is an end view of the proximal end of the intermediate member illustrated in FIG. 9.

FIG. 12 is an end view of the distal end of the intermediate member illustrated in FIG. 9.

FIG. 13 is a bottom view of the intermediate member illustrated in FIG. 9.

FIG. 14 is a perspective view of the intermediate member and tubular member illustrated in FIG. 9. The intermediate member and tubular member illustrated in FIG. 14 are in a first configuration.

FIG. 15 a perspective view of the intermediate member and tubular member illustrated in FIG. 9. The intermediate member and the tubular member illustrated in FIG. 15 are in a second configuration.

DETAILED DESCRIPTION

Figure 4:
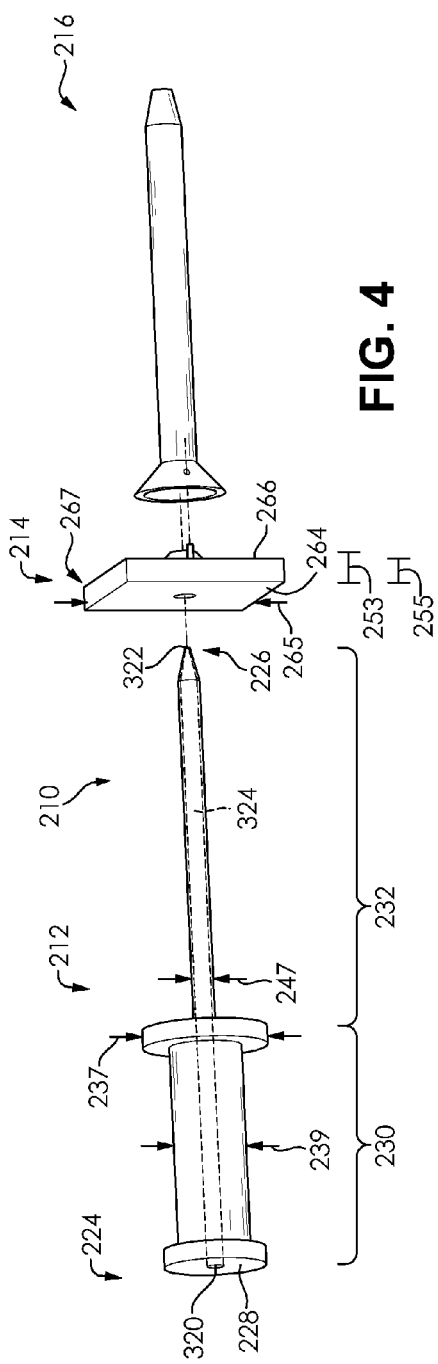
FIG. 4 is an exploded perspective view of another embodiment of a medical device.

The following detailed description and the appended drawings describe and illustrate various example embodiments of medical devices that have a releasable intermediate member and tubular member. In addition, example methods of treatment are described and illustrated. The description and illustration of these examples are provided to enable one skilled in the art to make and use a medical device for the treatment of a bodily passage and/or practice a method of using a medical device to treat a bodily passage. They are not intended to limit the scope of the claims in any manner.

The use of "e.g.," "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present or occur, and that the description includes instances where said element, event, feature, or circumstance occurs and instances where it does not. The use of "attached" refers to the fixed, releasable, or integrated association of two or more elements and/or devices. As used herein, the terms "proximal" and "distal" are used to describe opposing axial ends of the particular element or feature being described. The use of "diameter" refers to the length of a straight line passing from side to side through the center of a body, element, or feature, and does not impart any structural configuration on the body, element, or feature. The term "cuboid," or variations thereof, does not require that each side of the element or component be square and only requires that the element or component have six surfaces, hypothetical or actual, at right angles to each other. The term "bodily passage" or "body passage" refers to any passage within the body of an animal, including, but not limited to, humans, and includes elongate passages. The term "salivary duct" refers to parotid ducts (e.g., Stensen ducts), submandibular ducts (e.g., Wharton ducts), and/or sublingual ducts. The term "urinary tract" refers to the kidneys, renal pelvis, ureters, bladder, urethra, and/or any other portion of the urinary system. The term "medication" refers to any fluid, drug, agent, therapeutic agent, and/or any other material used to treat a patient.

FIGS. 1, 2, and 3 illustrate a medical device 10 that comprises an elongate member 12, an intermediate member 14, and a tubular member 16. The medical device 10 has a proximal end 18 and a distal end 20. When assembled, as shown in FIG. 1, each of the intermediate member 14 and tubular member 16 is releasably disposed on the elongate member 12, as described in more detail herein.

In the illustrated embodiment, the elongate member 12 comprises a proximal end 24, a distal end 26, a length 27, and a body 28 that defines a proximal portion 30 and a shaft 32. The length 27 of the elongate member 12 extends from the proximal end 24 to the distal end 26 of the elongate member 12.

The proximal portion 30 has a proximal end 34, a distal end 36, a length 35, a first outside diameter 37, a second outside diameter 39, and a third outside diameter 41. The length 35 of the proximal portion 30 extends from the proximal end 34 to the distal end 36 of the proximal portion 30. The first outside diameter 37 is disposed at the distal end 36 of the proximal portion 30, the second outside diameter 39 is disposed between the proximal end 34 and the distal end 36 of the proximal portion 30, and the third outside diameter 41 is disposed on the proximal end 34 of the proximal portion 30. Each of the first outside diameter 37 and the third outside diameter 41 is greater than the second outside diameter 39. The body 28 of the elongate member 12 defines the first outside diameter 37 along a first portion 38 of the proximal portion 30, the second outside diameter 39 along a second portion 40 of the proximal portion 30, and the third outside diameter 41 along a third portion 42 of the proximal portion 30. The first portion 38 extends from the distal end 36 toward the proximal end 34 to the second portion 40 and has a length that is less than the length 35 of the proximal portion 30. The second portion 40 extends from the first portion 38 to the third portion 42 and has a length that is less than the length 35 of the proximal portion 30. The third portion 42 extends from the second portion 40 to the proximal end 34 of the proximal portion 30 and has a length that is less than the length 35 of the proximal portion 30. The second portion 40 has a length that is greater than the length of the first portion 38 and the third portion 42.

The shaft 32 extends distally from the distal end 36 of the proximal portion 30 and has a proximal end 44, a tapered distal end 46, a first outside diameter 47 at the proximal end 44 of the shaft 32, and a second outside diameter 49 at the distal end 46 of the shaft 32. The shaft 32 has a length 45 that extends from the proximal end 44 to the distal end 46 of the shaft 32. The proximal end 44 of shaft 32 is attached to the distal end 36 of the proximal portion 30 and extends away from the proximal end 34 of the proximal portion 30. The first outside diameter 47 of the shaft 32 is greater than the second outside diameter 49 of the shaft 32. The first outside diameter 47 is less than the first outside diameter 37 of the proximal portion 30. The body 28 of the elongate member 12 defines the first outside diameter 47 along a first portion 48 of the shaft 32 that extends from the proximal end 44 of the shaft 32 toward the distal end 46 of the shaft 32. The first outside diameter 47 is constant along the first portion 48 of the shaft 32. The first outside diameter 47 of the shaft 32 tapers to the second outside diameter 49 along a second portion 50 of the shaft 32 that extends from the first portion 48 to the distal end 46 of the shaft 32. The first portion 48 has a length that is less than the length 45 of the shaft 32 and greater than the length of the second portion 50.

In the illustrated embodiment, the length 27 of the elongate member 12 is equal to the sum of the length 35 of the proximal portion 30 and the length 45 of the shaft 32. The length 35 of the proximal portion 30 is less than the length 45 of the shaft 32.

While the elongate member 12 has been illustrated as having a particular structural arrangement, an elongate member can have any suitable structural arrangement. Skilled artisans will be able to select a suitable structural arrangement for an elongate member according to a particular embodiment based on various considerations, including the structural arrangement of an intermediate member and/or tubular member included in a medical device of which the elongate member is a component. Example structural arrangements considered suitable for the proximal portion of an elongate member include a proximal portion that has an outside diameter that is constant, or substantially constant, along a portion, or the entirety, of its length, a proximal portion that has an outside diameter along a portion, or the entirety, of its length that is equal to, or substantially equal to, the first outside diameter, or any outside diameter, of a shaft, a proximal portion that has an outside diameter that is equal to, or substantially equal to, the first outside diameter of a shaft and that defines one or more protuberances that extend outward and away from the body of the elongate member (e.g., each protuberance providing a mechanical stop to proximal advancement of an intermediate portion and/or tubular member along the elongate member), and any other structural arrangement considered suitable for a particular application. Example structural arrangements considered suitable for the shaft of an elongate member include a shaft that has a constant, or substantially constant, outside diameter along a portion, or the entirety, of its length, a shaft that omits the inclusion of a tapered distal end, a shaft that has a diameter that varies along a portion, or the entirety, of its length, and any other structural arrangement considered suitable for a particular application. Optionally, an elongate member can define a lumen that extends through the proximal portion and the shaft, as shown in FIG. 4.

The shaft 32 can be attached to the distal end 36 of proximal portion 30 using any suitable technique or method of attachment. Skilled artisans will be able to select a suitable technique or method of attachment to use between the shaft and the proximal portion of an elongate member according to a particular embodiment based on various considerations, including the material(s) that forms the proximal portion and/or the shaft. Examples of suitable techniques and methods of attachment considered suitable between the proximal portion and the shaft of an elongate member include using an adhesive, welding, fusing (e.g., heat fusing), threaded connections, integrated components, and any other technique or method of attachment considered suitable for a particular application.

The elongate member 12 can be formed of any suitable material. Skilled artisans will be able to select a suitable material to form an elongate member according to a particular embodiment based on various considerations, including the material(s) that forms an intermediate member and/or a tubular member included in a medical device of which the elongate member is a component. Example materials considered suitable to form an elongate member include biocompatible materials, materials that can be made biocompatible, metals such as stainless steel, titanium, nickel-titanium alloy (e.g., Nitinol), polymers, Pebax (Pebax is a registered trademark of Ato Chimie Corporation of Allee des Vosges, Courbevoie, France), nylon, polyethylene, polyurethane, silicone, and any other material considered suitable for a particular application.

When assembled, as shown in FIG. 1, the intermediate member 14 is releasably disposed on shaft 32 and comprises a proximal end 52, a distal end 54, and a body 56. The intermediate member 14 has a length 53 that extends from the proximal end 52 to the distal end 54. The body 56 of the intermediate member 14 defines a first opening 58, a second opening 60, a lumen 62, a first surface 64, a second surface 66, a protuberance 68, and a support post 70. The first opening 58 is defined on the proximal end 52 and the second opening 60 is defined on the distal end 54. The lumen 62 extends from the first opening 58 to the second opening 60. Each of the first opening 58, second opening 60, and lumen 62 has an inside diameter that is sized and configured to receive the shaft 32. For example, each of the first opening 58, second opening 60, and lumen 62 has an inside diameter that is less than the first outside diameter 37 of the proximal portion 30 and greater than the first outside diameter 47 of the shaft 32.

The first surface 64 is opposably facing the second surface 66. The first surface 64 is disposed on the proximal end 52 of intermediate member 14 and the second surface 66 is disposed between the proximal end 52 and the distal end 54 of the intermediate member 14. A first portion 55 of the intermediate member 14 extends from the first surface 64 to the second surface 66. The first surface 64 and the second surface 66 cooperatively define a disc-shaped portion 67 of the intermediate member 14. The first surface 64 is circular and has an outside diameter 65 that is greater than the first outside diameter 37 of the proximal portion 30. The second surface 66 is circular and has an outside diameter that is equal to the outside diameter 65 of the first surface 64. While the first surface 64 has been illustrated as having an outside diameter that is equal to the outside diameter of the second surface 66, a first surface can have an outside diameter that is greater than, less than, or substantially equal to, the outside diameter of a second surface of an intermediate member.

The protuberance 68 extends distally from the second surface 66 and tapers from the second surface 66 to the distal end 54 of the intermediate member 14. In the illustrated embodiment, the protuberance 68 is frustoconical and the second opening 60 is defined on the protuberance 68. The protuberance 68 is complementary to a proximal portion 94 of the lumen 86 of the tubular member 16, as described in more detail herein. The support post 70 extends from the protuberance 68 and away from the second surface 66 to a support post end 72 and has an outside diameter that is constant along the length of the support post 70. In the illustrated embodiment, the support post 70 is cylindrical.

The intermediate member 14 can be formed of any suitable material. Skilled artisans will be able to select a suitable material to form an intermediate member according to a particular embodiment based on various considerations, including the material(s) that forms an elongate member and/or a tubular member included in a medical device of which the intermediate member is a component. Example materials considered suitable to form an intermediate member include biocompatible materials, materials that can be made biocompatible, metals such as stainless steel, titanium, nickel-titanium alloy (e.g., Nitinol), polymers, Pebax (Pebax is a registered trademark of Ato Chimie Corporation of Allee des Vosges, Courbevoie, France), nylon, polyethylene, polyurethane, polyetheretherketone (PEEK), silicone, and any other material considered suitable for a particular application. Optionally, an intermediate member can be formed of a material that is flexible relative to a material that forms an elongate member and/or tubular member (e.g., intermediate member is formed of a material that is relatively more flexible than a material that forms an elongate member and/or tubular member).

While the intermediate member 14 has been illustrated as having a particular structural arrangement, an intermediate member can have any suitable structural arrangement. Skilled artisans will be able to select a suitable structural arrangement for an intermediate member according to a particular embodiment based on various considerations, including the structural arrangement of an elongate member and/or tubular member included in a medical device of which the intermediate member is a component. Example structural arrangements considered suitable for an intermediate member include intermediate members that omit the inclusion of a protuberance, intermediate members that omit the inclusion of a support post, intermediate members that omit the inclusion of a protuberance and a support post, intermediate members that define a notch, opening, and/or slot that are sized and configured to receive a portion of a tubular member, intermediate members that define a recess that is sized and configured to receive a portion of an elongate member (e.g., protuberance), and any other structural arrangement considered suitable for a particular application.

While the first surface 64 has been illustrated as opposably facing the second surface 66, the first surface of an intermediate member can be positioned such that it is substantially opposably facing the second surface of an intermediate member, or disposed at an angle to the second surface of an intermediate member. Skilled artisans will be able to select a suitable arrangement between the first surface and second surface of an intermediate member according to a particular embodiment based on various considerations, including the structural arrangement of an elongate member and/or tubular member in a medical device of which the intermediate member is a component.

While the first surface 64 and the second surface 66 have been illustrated as cooperatively defining a disc-shaped portion 67 of the intermediate member 14, the first surface and/or second surface of an intermediate member can have any suitable structural configuration. Skilled artisans will be able to select a suitable structural configuration for the first surface and/or second surface of an intermediate member according to a particular embodiment based on various considerations, including the structural arrangement of an elongate member and/or tubular member included in a medical device of which the intermediate member is a component. Example structural configurations considered suitable for a first surface and/or second surface of an intermediate member include a first surface and/or second surface that is circular, square, triangular, rectangular, oval, curved, and any other structural configuration considered suitable for a particular application. The portion of an intermediate member that is cooperatively defined by the first surface and the second surface of an intermediate member can have any suitable geometric shape, such as a disc, cylinder, cuboid, cube, triangular prism, sphere, semi-sphere, and any other shape considered suitable for a particular application (e.g., such that a portion of an intermediate member extends beyond the outside diameter of the proximal portion of an elongate member when assembled).

While each of the first opening 58, second opening 60, and lumen 62 has been illustrated as having an inside diameter that is greater than the first outside diameter 47 of shaft 32, the first opening, second opening, and/or lumen of an intermediate member can have any suitable diameter, such as a diameter that is greater than, equal to, substantially equal to, or less than the first outside diameter of a shaft. For example, when an intermediate member is formed of a material that is relatively more flexible than a material that forms an elongate member, a first opening, second opening, and/or lumen can have a diameter that is equal to, substantially equal to, or less than the first outside diameter of a shaft. In these embodiments, the first opening, second opening, and/or lumen can expand when the shaft is passed through, or disposed within, the first opening, second opening, and/or lumen to provide a friction fit between the two components.

While the intermediate member 14 has been illustrated as having a frustoconical protuberance 68, the body of an intermediate member can define a protuberance that has any suitable structural arrangement. Skilled artisans will be able to select a suitable structural arrangement for the protuberance of an intermediate member according to a particular embodiment based on various considerations, including the structural arrangement of a tubular member included in a medical device of which the intermediate member is a component. Example structural arrangements considered suitable for a protuberance of an intermediate member include a protuberance that extends along a portion, or the entirety, of the circumference of an opening defined by the body of the intermediate member, a protuberance that defines one or more edges, a protuberance that has a constant, or substantially constant, outside diameter along a portion, or the entirety, of its length, a protuberance that is a cylinder, cuboid, cube, triangular prism, sphere, semi-sphere, and any other structural arrangement considered suitable for a particular application.

While the intermediate member 14 has been illustrated as having a cylindrical support post 70, an intermediate member can have any suitable number of support posts and each support post can have any suitable structural arrangement. Skilled artisans will be able to select a suitable structural arrangement for a support post and a suitable number of support posts to include on an intermediate member according to a particular embodiment based on various considerations, including the structural arrangement of a tubular member included in a medical device of which the intermediate member is a component. Example structural arrangements considered suitable for a support post include a support post that has a constant, or substantially constant, outside diameter along a portion, or the entirety, of its length, a support post that has a diameter that varies along its length, a support post that includes one or more protuberances along its length to assist with attachment to a tubular member, a support post that has a geometric shape, such as a cylinder, cuboid, cube, triangular prism, sphere, semi-sphere, and any other structural arrangement considered suitable for a particular application. Example number of support posts considered suitable to include on an intermediate member include one, at least one, two, a plurality, three, four, five, six, seven, and any other number considered suitable for a particular application. In embodiments in which one or more support posts are included, each support post can extend from the second surface of an intermediate member and/or from a protuberance defined by the body of the intermediate member.

When assembled, as shown in FIG. 1, the tubular member 16 is releasably disposed on the shaft 32 distal to the intermediate member 14. The tubular member 16 comprises a proximal end 76, a distal end 78, and a body 80. The tubular member has a length 77 that extends from the proximal end 76 to the distal end 78 and is less than the length 45 of shaft 32. The body 80 of the tubular member 16 defines a first opening 82, a second opening 84, a lumen 86, a flared proximal portion 88, a tapered distal portion 90, and a passageway 92. The first opening 82 is defined on the proximal end 76 and the second opening 84 is defined on the distal end 78. The lumen 86 extends from the first opening 82 to the second opening 84.

The first opening 82 has a first inside diameter 79 and the second opening 84 has a second inside diameter 81. Thus, the lumen 86 has a first inside diameter 79 and a second inside diameter 81. The first inside diameter 79 is greater than the second inside diameter 81 and is greater than the first outside diameter 47 of the shaft 32. The second inside diameter 81 is greater than the first outside diameter 47 of the shaft 32. Alternatively, the second inside diameter of a tubular member can be equal to, substantially equal to, or less than the first outside diameter of a shaft such that a friction fit between the tubular member and shaft can be accomplished. The first inside diameter 79 tapers to the second inside diameter 81 along a first portion 83 of the tubular member 16 that extends from the proximal end 76 toward the distal end 78 to a location between the proximal end 76 and the distal end 78. The second inside diameter 81 extends along a second portion 85 of the tubular member 16 that extends from the first portion 83 to the distal end 78 of the tubular member 16. The lumen 86 has a proximal portion 94 that has a structural arrangement that is complementary to the structural arrangement of the protuberance 68 of the intermediate member 14 and is sized and configured to receive the protuberance 68 such that the proximal end 76 of the tubular member 16 contacts the intermediate member 14 (e.g., second surface 66) when the device is assembled. Alternatively, the proximal portion of the lumen of a tubular member can be sized and configured to receive a portion of a protuberance defined by an intermediate member such that the proximal end of the tubular member does not contact the intermediate member (e.g., second surface 66) when the device is assembled. The proximal portion 94 of lumen 86 is frustoconical and tapers from the proximal end 76 of the tubular member 16 toward the distal end 78.

The tubular member 16 has a first outside diameter 87, a second outside diameter 89, and a third outside diameter 91. The first outside diameter 87 is disposed on the proximal end 76, the second outside diameter 89 is disposed along a portion of the length 77 between the proximal end 76 and the distal end 78, and the third outside diameter 91 is disposed on the distal end 78. The first outside diameter 87 is greater than the second outside diameter 89 and is disposed proximal to the second outside diameter 89. The second outside diameter 89 is greater than the third outside diameter 91 and is disposed proximal to the third outside diameter 91. The first outside diameter 87 tapers to the second outside diameter 89 along a third portion 96 of the tubular member 16 that extends from the proximal end 76 toward the distal end 78 and defines the flared proximal portion 88. The flared proximal portion 88 acts as a mechanical stop to distal advancement of the tubular member 16 beyond tissue disposed outside of a bodily passage (e.g., the flared proximal portion contacts tissue disposed outside of a bodily passage). The flared proximal portion 88 is frustoconical and tapers from the proximal end 76 of the tubular member 16 toward the distal end 78. The second outside diameter 89 extends along a fourth portion 100 of the tubular member 16 that extends from the third portion 96 toward the distal end 78. The second outside diameter 89 tapers to the third outside diameter 91 along a fifth portion 102 of the tubular member 16 and defines the tapered distal portion 90.

The passageway 92 is disposed on the flared proximal portion 88 of tubular member 16 between the proximal end 76 and the distal end 78 of the tubular member 16. The passageway 92 extends through the body 80 of the tubular member 16 on the flared proximal portion 88 and provides access to lumen 86. The passageway 92 has a diameter that is sized and configured to receive support post 70. For example, the passageway 92 can have a diameter that is greater than the outside diameter of support post 70. The passageway 92 can have any suitable structural arrangement, such as a structural arrangement that is complementary to the structural arrangement of a support post defined by the body of an intermediate member. For example, a passageway can have a structural arrangement that defines any suitable geometric shape, such as a cylinder, cuboid, cube, triangular prism, sphere, semi-sphere, and any other structural arrangement considered suitable for a particular embodiment. In the illustrated embodiment, passageway 92 is cylindrical.

While the tubular member 16 has been illustrated as having a particular structural arrangement, a tubular member can have any suitable structural arrangement. Skilled artisans will be able to select a suitable structural arrangement for a tubular member according to a particular embodiment based on various considerations, including the structural arrangement of an elongate member and/or intermediate member included in a medical device of which the tubular member is a component. Example structural arrangements considered suitable for a tubular member include tubular members that omit the inclusion of a flared proximal portion, tubular members that omit the inclusion of a tapered distal end, tubular members that omit the inclusion of a flared proximal portion and a tapered distal end, tubular members that define a shoulder, or stepped, configuration alternative to a flared proximal portion, tubular members that have a constant, or substantially constant, outside diameter along a portion, or the entirety, of their length, tubular members in which a lumen defined by the tubular member has a constant, or substantially constant, inside diameter along a portion, or the entirety, of its length, and any other structural arrangement considered suitable for a particular application. For example, a tubular member, such as those described herein, can include a completely circumferentially closed member, a member that defines a slit along the entirety, or a portion, of its length, a member that defines one or more, or a plurality, of perforations along its length, a sheath, and any other structural configuration considered suitable for a particular embodiment.

While the body 80 of the tubular member 16 has been illustrated as defining a passageway 92 that extends through the body 80 of the tubular member 16 on the flared proximal portion 88 of the tubular member 16, the body of a tubular member can define any suitable number of passageways and each passageway can extend through any suitable portion of a tubular member. Skilled artisans will be able to select a suitable number of passageways to define on a tubular member and a suitable location to position each passageway according to a particular embodiment based on various considerations, including the number of support posts defined by an intermediate member included in a medical device of which the tubular member is a component. Example number of passageways considered suitable to include on a tubular member include one, at least one, two, a plurality, three, four, five, six, seven, and any other number considered suitable for a particular application. Example locations considered suitable to define a passageway on a tubular member include on the flared proximal portion of a tubular member, between the proximal end and the distal end of a tubular member, on the tapered distal portion of a tubular member, and any other location considered suitable for a particular application.

A passageway defined by a tubular member can have any suitable diameter, such as a diameter that is greater than, equal to, substantially equal to, or less than the outside diameter of a support post defined by an intermediate member. For example, when a tubular member is formed of a material that is relatively more flexible than a material that forms an intermediate member, a passageway can have a diameter that is equal to, substantially equal to, or less than the diameter of a support post. In these embodiments, the passageway can expand when the support post is passed through, or disposed within, the passageway to provide a friction fit between the two components.

The tubular member 16 can be formed of any suitable material. Skilled artisans will be able to select a suitable material to form a tubular member according to a particular embodiment based on various considerations, including the material(s) that forms an elongate member and/or an intermediate member included in a medical device of which the tubular member is a component. Example materials considered suitable to form a tubular member include biocompatible materials, materials that can be made biocompatible, biodegradable materials, bioabsorbable materials such as chitosan, metals such as stainless steel, titanium, nickel-titanium alloy (e.g., Nitinol), polymers, Pebax (Pebax is a registered trademark of Ato Chimie Corporation of Allee des Vosges, Courbevoie, France), nylon, polyethylene, polyurethane, polytetrafluoroethylene (PTFE), silicone, and any other material considered suitable for a particular application.

Optionally, a tubular member can have a first portion that is relatively more rigid than a second portion when the tubular member is free of the elongate member and/or intermediate member included in a medical device of which the tubular member is a component. Thus, the second portion can be relatively more flexible than the first portion. The first portion can extend from the proximal end toward the distal end to a location disposed between the proximal end and the distal end. The second portion can extend from the location disposed between the proximal end and the distal end to the distal end of the tubular member. The first portion can be formed of a first material and the second portion can be formed of a second material. The first material can be the same as, or different than, the second material. For example, the first portion can be formed of a material that has a first durometer hardness and the second portion can be formed of a material that has a second durometer hardness. The second durometer hardness is less than the first durometer hardness. For example, a tubular member can have a distal end, or a distal portion that extends from the distal end toward the proximal end, that has a second durometer hardness that is less than a first durometer hardness at the proximal end, or along a proximal portion that extends from the proximal end toward the distal end. Optionally, a tubular member can have a flared proximal portion that has a first durometer hardness that is greater than a second durometer hardness of the portion of the tubular member that extends from the flared proximal portion to the distal end of the tubular member, or a location between the flared proximal portion and the distal end of the tubular member.

In embodiments in which the first portion is formed of a first material that is different than a second material that forms the second portion, the first portion and the second portion can be attached to one another using any suitable technique or method of attachment. Examples of suitable techniques and methods of attachment considered suitable to attach a first portion and a second portion of a tubular member include using an adhesive, welding, fusing (e.g., heat fusing), threaded connections, and any other technique or method of attachment considered suitable for a particular application.

When the medical device 10 is fully assembled, as illustrated in FIG. 1, the distal end 78 of the tubular member 16 is disposed proximal to the distal end 26 of the elongate member 12. In the illustrated embodiment, the second portion 50 of the shaft 32 is disposed distal to the distal end 78 of the tubular member 16. In addition, the fifth portion 102 of tubular member 16 is disposed proximal to the second portion 50 of the shaft 32. This structural arrangement provides an assembled medical device 10 that has a tapered distal end and provides a mechanism for reducing the trauma to a bodily passage as the medical device 10 is advanced into the bodily passage. Alternatively, a portion of the second portion of a shaft can be disposed distal to the distal end of a tubular member and/or a portion of the fifth portion of a tubular member can be disposed proximal to the a second portion of a shaft.

When the medical device 10 is fully assembled, the intermediate member 14 is releasably disposed on the shaft 32 between the distal end 36 of the proximal portion 30 and the proximal end 76 of the tubular member 16. Thus, the intermediate member 14 is disposed between the proximal portion 30 and the tubular member 16. The tubular member 16 is releasably disposed on the shaft 32 and is disposed distal to the intermediate member 14 such that the protuberance 68 is disposed within the proximal portion 94 of the lumen 86 and the support post 70 of the intermediate member 14 is disposed through the passageway 92 defined by the body 80 of tubular member 16. The support post 70 has a length such that the support post end 72 is disposed distal to the passageway 92 defined by the tubular member 16. The lengthwise axis of the support post 70 is coaxial with the lengthwise axis of the passageway 92. Alternatively, a portion of a protuberance of an intermediate member can be disposed within the proximal portion of the lumen of a tubular member, a support post (e.g., support post end) can be disposed within a passageway defined by the body of a tubular member, and/or a support post can be positioned such that its lengthwise axis is not coaxial with the lengthwise axis of the passageway when the device is assembled. When a support post defined by an intermediate member is disposed within, or through, a passageway defined by a tubular member, the tubular member is rotationally fixed relative to the intermediate member.

In the illustrated embodiment, the first outside diameter 65 of the first surface 64 is greater than the first outside diameter 37 of the proximal portion 30. This structural arrangement provides a pushing surface (e.g., the length of the first surface 64 that extends beyond the first outside diameter 37 of the proximal portion 30) that can be used to remove the intermediate member 14 and/or the tubular member 16 from the elongate member 12 during use. For example, after a portion of the medical device 10 (e.g., portion of shaft, portion of tubular member) has been introduced into a bodily passage, salivary duct, or a portion of the urinary tract, a distally-directed force (e.g., toward the bodily passage) can be applied on the intermediate member 14 (e.g., first surface 64) to advance the intermediate member 14 and the tubular member 16 distally along the shaft 32 until each of the intermediate member 14 and tubular member 16 becomes free of the elongate member 12. Alternatively, after a portion of the medical device 10 (e.g., portion of shaft, portion of tubular member) has been introduced into a bodily passage, the position of the intermediate member 14 can be maintained, and/or a distally-directed force can be applied to the intermediate member, relative to the tissue disposed outside of the bodily passage and/or the bodily passage while a proximally-directed force is applied on the elongate member 12 (e.g., proximal portion) to advance the elongate member 12 proximally until it becomes free of the intermediate member 14 and the tubular member 16. The tubular member 16 can be used to complete treatment on, or within, the bodily passage and can be left in the bodily passage for an interval of time, or removed subsequent to the treatment being performed. Optionally, the tubular member 16 can be sutured to the tissue disposed outside of the bodily passage and/or the bodily passage wall. This can be accomplished, for example, by using passageway 92, or any other passageway defined by the body of the tubular member.

Each of the elongate member 12, intermediate member 14, and tubular member 16 can be fabricated using any suitable technique or method of manufacture. Skilled artisans will be able to select a suitable technique or method of manufacture to fabricate an elongate member, intermediate member, and/or tubular member according to a particular embodiment based on various considerations, including the material(s) that forms each component. Example techniques and methods of manufacture considered suitable to fabricate an elongate member, intermediate member, and/or a tubular member include extrusion processes, molding processes, and any other technique or method considered suitable for a particular application.

FIG. 3A illustrates an alternative elongate member 12' and an alternative intermediate member 14'. The inclusion of a tubular member has been omitted from FIG. 3A for clarity. The elongate member 12' is similar to the elongate member 12 illustrated in FIGS. 1, 2, and 3 and described above, except as detailed below. The intermediate member 14' is similar to the intermediate member 14 illustrated in FIGS. 1, 2, and 3 and described above, except as detailed below.

The illustrated elongate member 12' has a body 28' that defines a protuberance 110' between the proximal end 44' of the shaft 32' and the distal end 46' of the shaft 32'. The protuberance 110' extends outward and away from the shaft 32' and has an outside diameter 111' that is greater than the first outside diameter 47' of the shaft 32'. While the protuberance 110' is described as being defined by the body 28' of the elongate member 12', a protuberance can alternatively be a separate component attached to the shaft of an elongate member using any suitable technique or method of attachment, such as welding, or by using adhesives.

While the elongate member 12' has been illustrated as having a protuberance 110', an elongate member can have any suitable number of protuberances, each having any suitable structural configuration. Skilled artisans will be able to select a suitable number of protuberances and a suitable structural arrangement for a protuberance according to a particular embodiment based on various considerations, including the structural arrangement of an intermediate member included in a medical device of which the elongate member is a component. Example number of protuberances considered suitable to include on an elongate member include one, at least one, two, a plurality, three, four, five, six, seven, and any other number considered suitable for a particular application. Example structural arrangements considered suitable for a protuberance include protuberances that extend about a portion, or the entirety, of the circumference of a shaft, protuberances that have an outside diameter that is greater than the first outside diameter of a shaft but less than the first outside diameter of the proximal portion of an elongate member, and any other structural arrangement considered suitable for a particular application.

The illustrated intermediate member 14' has a body 56' that defines a lumen 62' that has a recess 112' between the proximal end 52' and the distal end 54' of the intermediate member 14'. The recess 112' is sized and configured to receive the protuberance 110'. In the illustrated embodiment, the recess 112' has an inside diameter that is greater than the inside diameter of lumen 62'.

While the intermediate member 14' has been illustrated as having a recess 112', an intermediate member can have any suitable number of recesses, each having any suitable structural configuration. Skilled artisans will be able to select a suitable number of recesses and a suitable structural arrangement for a recess according to a particular embodiment based on various considerations, including the structural arrangement of an elongate member included in a medical device of which the intermediate member is a component. Example number of recesses considered suitable to include on an intermediate member include one, at least one, two, a plurality, three, four, five, six, seven, and any other number considered suitable for a particular application. Example structural arrangements considered suitable for a recess include recesses that extend about a portion, or the entirety, of the circumference of the lumen of an intermediate member, recesses that have an inside diameter that is greater than the inside diameter of the lumen of an intermediate member but less than the outside diameter of the first surface of an intermediate member, and any other structural arrangement considered suitable for a particular application. Optionally, an intermediate member can omit the inclusion of a recess.

In use, the protuberance 110' and the recess 112' provide a mechanism for releasably attaching intermediate member 14' to elongate member 12'. For example, the shaft 32' of the elongate member 12' can be passed through the lumen 62' defined by the intermediate member 14' such that the protuberance 110' is disposed within recess 112'. The intermediate member 14' can be formed of a material that is relatively more flexible than a material that forms elongate member 12' such that the lumen 62' defined by the intermediate member 14' can expand when the protuberance 110' is passed through the portion of lumen 62' disposed proximal to the recess 112'. Alternatively, an elongate member, or a portion of the elongate member (e.g., protuberance), can be formed of a material that is relatively more flexible than a material that forms an intermediate member such that the protuberance compresses until it is disposed within a recess defined by the intermediate member.

FIG. 4 illustrates another medical device 210. The medical device 210 is similar to the medical device 10 illustrated in FIGS. 1, 2, and 3 and described above, except as detailed below. Thus, the medical device 210 comprises an elongate member 212, an intermediate member 214, and a tubular member 216.

In this embodiment, the body 228 of the elongate member 212 defines a first opening 320, a second opening 322, and a lumen 324. The first opening 320 is disposed on the proximal end 224 of the elongate member 212. The second opening 322 is disposed on the distal end 226 of the elongate member 212. The lumen 324 extends from the first opening 320 to the second opening 322 and through the proximal portion 230 and the shaft 232. Each of the first opening 320, the second opening 322, and the lumen 324 has an inside diameter that is less than the second outside diameter 239 of proximal portion 230 and the first outside diameter 247 of the shaft 232. Any suitable device can be passed through the lumen 324, such as a guide wire. Alternatively, any suitable device can be disposed within the lumen defined by an elongate member.

In this embodiment, the first surface 264 and the second surface 266 of the intermediate member 214 cooperatively define a cuboid portion 267 of the intermediate member 214 in which each of the first surface 264 and second surface 266 are square. A first portion 255 of the intermediate member 214 extends from the first surface 264 to the second surface 266. The first portion 255 of the intermediate member 214 has a length that is less than the length 253 of the intermediate member 214. The first surface 264 has an outside diameter 265 that is greater than the first outside diameter 237 of the proximal portion 230 and the second surface 266 has an outside diameter that is equal to the outside diameter 265 of the first surface 264.

Figure 5:
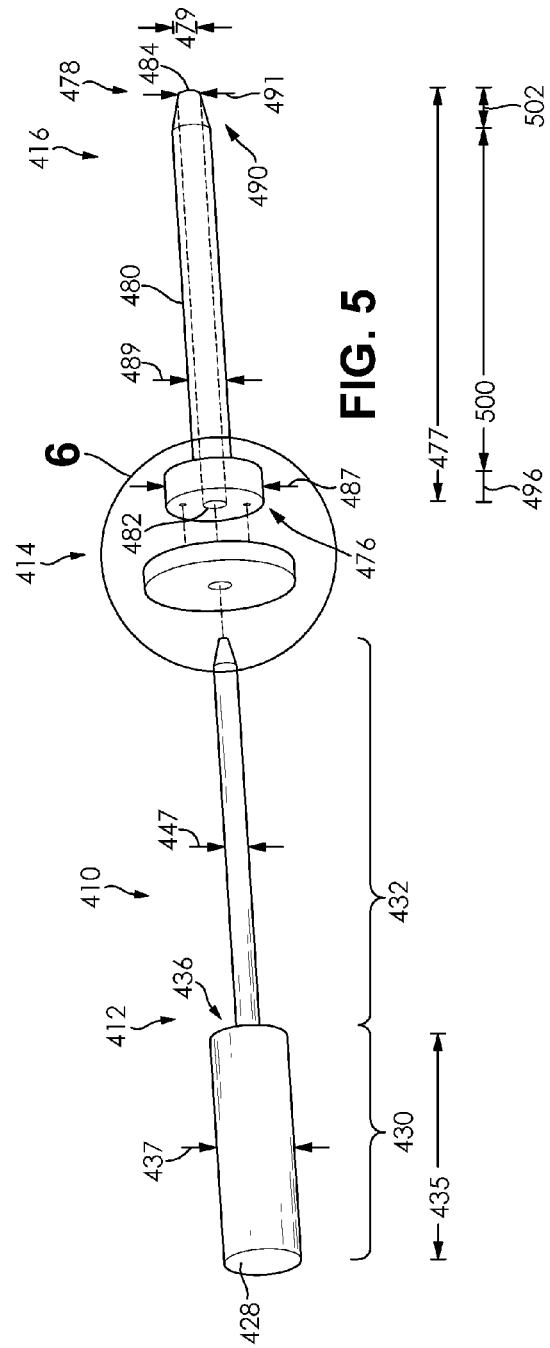
FIG. 5 is an exploded perspective view of another embodiment of a medical device.
Figure 6:
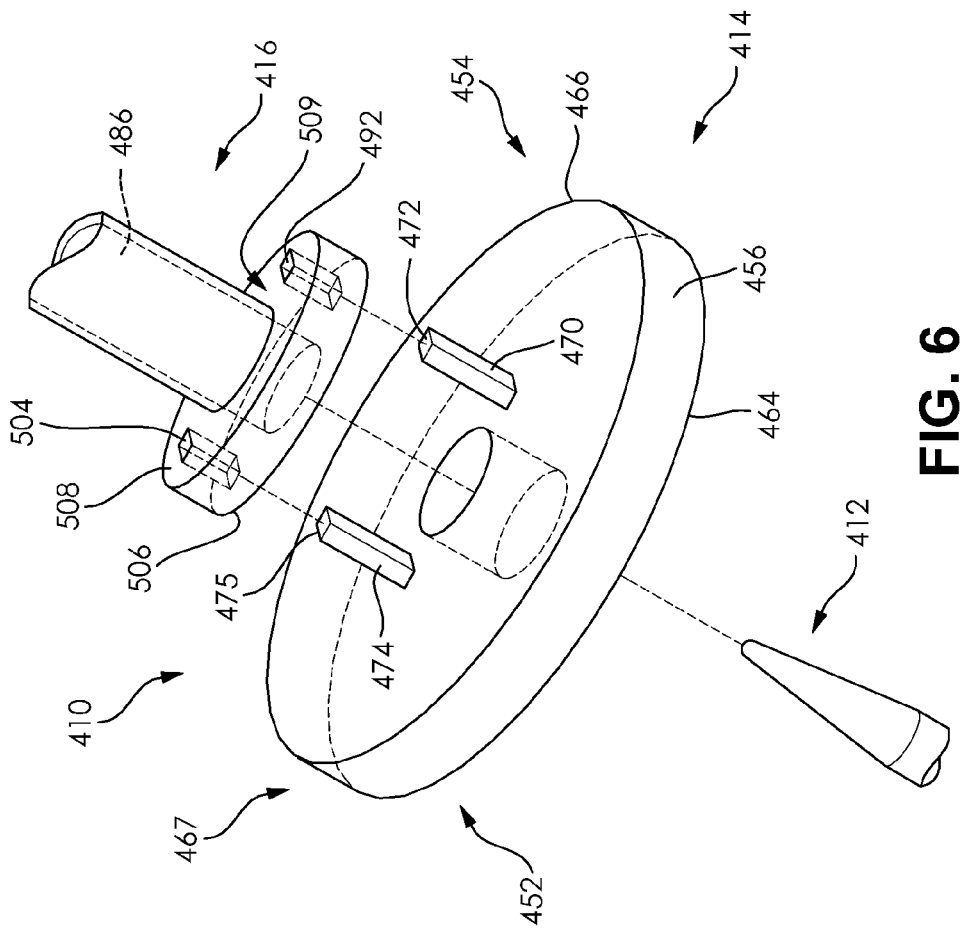
FIG. 6 is a magnified view of area 6 illustrated in FIG. 5.

FIGS. 5 and 6 illustrate another medical device 410. The medical device 410 is similar to the medical device 10 illustrated in FIGS. 1, 2, and 3 and described above, except as detailed below. Thus, the medical device 410 comprises an elongate member 412, an intermediate member 414, and a tubular member 416.

In the illustrated embodiment, the elongate member 412 has a body 428 that defines a proximal portion 430 and a shaft 432 that extends distally from the distal end 436 of the proximal portion 430. The proximal portion 430 has an outside diameter 437 that is constant along the length 435 of the proximal portion 430. The outside diameter 437 of the proximal portion 430 is greater than the first outside diameter 447 of the shaft 432.

In the illustrated embodiment, the intermediate member 414 omits the inclusion of a protuberance (e.g., protuberance 68) and the body 456 of the intermediate member 414 defines a first support post 470 and a second support post 474. The first surface 464 is disposed on the proximal end 452 of the intermediate member 414 and the second surface 466 is disposed on the distal end 454 of the intermediate member 414. The first support post 470 extends from the second surface 466 and away from the first surface 464 to a first support post end 472 and the second support post 474 extends from the second surface 466 and away from the first surface 464 to a second support post end 475. Each of the first support post 470 and second support post 474 is cuboidal. In the illustrated embodiment, the first support post 470 has a length that is equal to the length of the second support post 474. The first support post 470 has a first lengthwise axis that extends through its length that is parallel to a second lengthwise axis that extends through the length of the second support post 474. However, other structural arrangements are considered suitable, such as structural arrangements in which the first lengthwise axis is substantially parallel, or not parallel, to the second lengthwise axis.

While the first support post 470 has been illustrated as having a length that is equal to the length of the second support post 474, a support post can have any suitable length. Skilled artisans will be able to select a suitable length for a support post according to a particular embodiment based on various considerations, including the structural arrangement of a tubular member included in a medical device of which the intermediate member is a component. Example lengths considered suitable for a support post include a first support post that has a length that is greater than, equal to, substantially equal to, or less than the length of a second support post.

In the illustrated embodiment, the tubular member 416 omits the inclusion of a flared proximal portion (e.g., flared proximal portion 88) and has a body 480 that defines a first opening 482, a second opening 484, a lumen 486, a tapered distal portion 490, a first passageway 492, a second passageway 504, a first surface 506, and a second surface 508. The first opening 482 is defined on the proximal end 476 and the second opening 484 is defined on the distal end 478. The lumen 486 extends from the first opening 482 to the second opening 484. Each of the first opening 482, second opening 484, and lumen 486 has an inside diameter 479 that is greater than the first outside diameter 447 of the shaft 432.

The first surface 506 is opposably facing the second surface 508. Alternatively, the first surface of a tubular member can be substantially opposably facing the second surface, or disposed at an angle to the second surface. The tubular member 416 has a first outside diameter 487, a second outside diameter 489, and a third outside diameter 491. The first outside diameter 487 is greater than the second outside diameter 489 and the second outside diameter 489 is greater than the third outside diameter 491. The first outside diameter 487 extends from the first surface 506 to the second surface 508. The first outside diameter 487 extends along a first portion 496 of the tubular member 416 that extends from the proximal end 476 to the second surface 508. The second outside diameter 489 extends along a second portion 500 of the tubular member 416 that extends from the first portion 496 (e.g., the second surface 508) toward the distal end 478. The second outside diameter 489 tapers to the third outside diameter 491 along a third portion 502 of the tubular member 416 that extends from the second portion 500 to the distal end 478 of the tubular member 416. This structural arrangement of the tubular member 416 defines a shoulder 509 between the proximal end 476 and the distal end 478 of the tubular member 416. During use, the shoulder 509 acts as a mechanical stop to distal advancement of the tubular member 416 beyond the tissue disposed outside of the bodily passage (e.g., the second surface 508 contacts the tissue disposed outside of the bodily passage).

The first passageway 492 extends from an opening defined on the first surface 506 to an opening defined on the second surface 508. The second passageway 504 extends from an opening defined on the first surface 506 to an opening defined on the second surface 508. The first passageway 492 has an inside diameter that is greater than the outside diameter of the first support post 470 and second passageway 504 has an inside diameter that is greater than the outside diameter of the second support post 474. Alternatively, the first passageway and/or second passageway defined by a tubular member can have an inside diameter that is equal to, substantially equal to, or less than the outside diameter of a support post such that a friction fit between the intermediate member and tubular member can be accomplished. The first passageway 492 has a structural arrangement that is complementary to the first support post 470 and the second passageway 504 has a structural arrangement that is complementary to the second support post 474. In the illustrated embodiment, each of the first passageway 492 and second passageway 504 is cuboidal. The first passageway 492 has a first lengthwise axis and the second passageway 504 has a second lengthwise axis. The first lengthwise axis is parallel to the second lengthwise axis. However, other structural arrangements are considered suitable, such as structural arrangements in which the first lengthwise axis is substantially parallel, or not parallel, to the second lengthwise axis.

When the medical device 410 is fully assembled, intermediate member 414 is releasably disposed on shaft 432 between the distal end 436 of the proximal portion 430 and the proximal end 476 of tubular member 416. Thus, intermediate member 414 is disposed between the proximal portion 430 and the tubular member 416. The tubular member 416 is releasably disposed on shaft 432 and is disposed distal to intermediate member 414 such that the first support post 470 is disposed through the first passageway 492 and the second support post 474 is disposed through the second passageway 504. The lengthwise axis of the first support post 470 is coaxial with the lengthwise axis of the first passageway 492 and the lengthwise axis of the second support post 474 is coaxial with the lengthwise axis of the second passageway 504. Alternatively, the lengthwise axis of the support post of an intermediate member can be disposed at an angle to the lengthwise axis of a passageway defined by a tubular member. When the first support post 470 is disposed through the first passageway 492 and the second support post 474 is disposed through the second passageway 504, the tubular member 416 is rotationally fixed relative to the intermediate member 414.

Various methods of treatment are described herein. While the methods described herein are shown and described as a series of acts, it is to be understood and appreciated that the methods are not limited by the order of acts, as some acts may in accordance with these methods, occur in different orders, and/or concurrently with other acts described herein.

Figure 7:
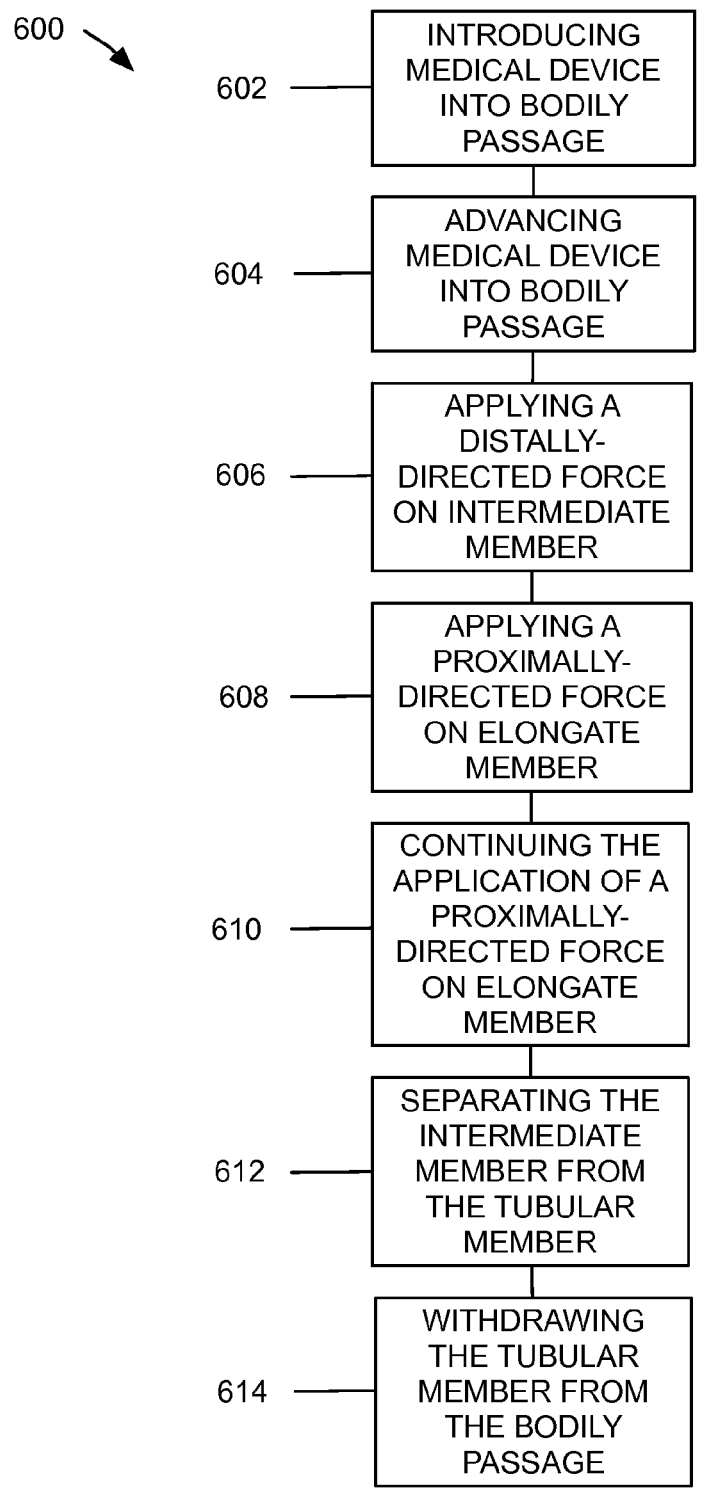
FIG. 7 is a flowchart representation of a method of treatment.

FIG. 7 is a flowchart representation of a method 600 of treating a bodily passage.

A step 602 comprises introducing a medical device having a medical device proximal end and a medical device distal end into a bodily passage such that the medical device distal end is disposed within the bodily passage. The bodily passage is defined by a bodily passage wall. Another step 604 comprises advancing the medical device into the bodily passage until the second outside diameter of the tubular member is disposed within the bodily passage. Another step 606 comprises applying a distally-directed force on the intermediate member. Another step 608 comprises applying a proximally-directed force on the elongate member while applying a distally-directed force on the intermediate member such that the elongate member is advanced proximally relative to the intermediate member and the tubular member. Another step 610 comprises continuing the application of a proximally-directed force on the elongate member while applying a distally-directed force on the intermediate member until the elongate member is free of the intermediate member and the tubular member. Another step 612 comprises separating the intermediate member from the tubular member. Another step 614 comprises withdrawing the tubular member from the bodily passage.

Step 602 can be accomplished using any suitable medical device according to an embodiment, such as the embodiments described and illustrated herein. Skilled artisans will be able to select a suitable medical device to introduce into a bodily passage according to a particular embodiment based on various considerations, including the treatment intended to be performed. Examples of medical devices considered suitable to introduce into a bodily passage to complete one or more steps and/or methods described herein include medical device 10, medical device 210, medical device 410, medical device 810, medical devices that include the alternative components described herein (e.g., elongate member 12', intermediate member 14', intermediate member 814', tubular member 1016), and any other medical device considered suitable for a particular application.

Step 602 can be accomplished by introducing a medical device into any suitable bodily passage. Skilled artisans will be able to select a suitable bodily passage to introduce a medical device according to a particular embodiment based on various considerations, including the treatment intended to be performed. Example bodily passages considered suitable to introduce a medical device include a salivary duct, a portion of the urinary tract, and any other bodily passage considered suitable for a particular application.

Step 604 can be accomplished by applying a distally-directed force (e.g., toward the bodily passage) on any suitable portion of the medical device such that the medical device is advanced into the bodily passage and the second outside diameter of the tubular member is disposed within the bodily passage. For example, a distally-directed force can be applied to an elongate member of an embodiment, such as elongate member 12, elongate member 12', elongate member 212, elongate member 412, or elongate member 812.

An optional step comprises advancing the medical device into the bodily passage such that the flared proximal portion of the tubular member contacts tissue disposed outside of the bodily passage. This step can be accomplished by placing a distally-directed force on any suitable portion of the medical device until the distal surface of the flared proximal portion contacts the tissue disposed outside of the bodily passage. Alternatively, if the tubular member omits the inclusion of a flared proximal portion, such as tubular member 416, an optional step comprises advancing the medical device into the bodily passage such that the second surface of the tubular member contacts tissue disposed outside of the bodily passage. This step can be accomplished by placing a distally-directed force on any suitable portion of the medical device until the distal surface of second surface of the tubular member contacts the tissue disposed outside of the bodily passage. Alternatively, if the tubular member defines a constant, or substantially constant diameter along a proximal portion of its length, an optional step comprises advancing the medical device into the bodily passage such that the proximal end of the tubular member is disposed adjacent, or near, an opening of the bodily passage. This step can be accomplished by placing a distally-directed force on any suitable portion of the medical device until the distal surface of second surface of the tubular member contacts the tissue disposed outside of the bodily passage.

Step 606 can be accomplished by applying a distally-directed force on the intermediate member such that the intermediate member is advanced toward and/or contacts the tissue disposed outside of the bodily passage. The distally-directed force can be applied to any suitable portion of an intermediate member, such as the outside perimeter, or edge, of the intermediate member, and/or the first surface of an intermediate member (e.g., first surface 64, first surface 264, first surface 464, first surface 864).

Alternative to applying a distally-directed force on the intermediate member, an alternative step comprises maintaining the position of the intermediate member relative to the tubular member. This step can be accomplished by applying any suitable force on the intermediate member such that the position of the intermediate member is maintained relative to the tubular member, the tissue disposed outside of the bodily passage, and/or the bodily passage.

Step 608 can be accomplished by applying a proximally-directed force (e.g., away from the bodily passage) on any suitable portion of the elongate member while applying a distally-directed force on the intermediate member such that the elongate member is advanced proximally relative to the intermediate member and tubular member and is advanced proximally through the lumen defined by the tubular member. For example, step 608 can be accomplished concurrently with step 606. Proximally-directed force can be applied to proximal portion 30, proximal portion 30', proximal portion 230, proximal portion 430, proximal portion 830, or any other portion of an elongate member considered suitable for a particular application.

Alternative to applying a proximally-directed force on the elongate member while applying a distally-directed force on the intermediate member, an alternative step comprises applying a proximally-directed force on the elongate member while maintaining the position of the intermediate member relative to the tubular member such that the elongate member is advanced proximally relative to the intermediate member and the tubular member and is advanced proximally through the lumen defined by the tubular member.

Step 610 can be accomplished by continuing the application of a proximally-directed force on the elongate member while applying a distally-directed force on the intermediate member until the distal end of the shaft is disposed proximal to the proximal end of the intermediate member and the elongate member is free of the tubular member and the intermediate member.

Alternative to continuing the application of a proximally-directed force on the elongate member while applying a distally-directed force on the intermediate member, an alternative step comprises continuing the application of a proximally-directed force on the elongate member while maintaining the position of the intermediate member relative to the tubular member until the distal end of the shaft is disposed proximal to the proximal end of the intermediate member and the elongate member is free of the intermediate member and the tubular member.

Step 612 can be accomplished by applying a proximally-directed force (e.g., away from the bodily passage) on any suitable portion of the intermediate member (e.g., disc-shaped portion 67, cuboid portion 267, disc-shaped portion 467) such that the support post is withdrawn from the passageway defined by the tubular member. Alternatively, if the intermediate member includes more than one support post and the tubular member defines more than one passageway (e.g., intermediate member 414, tubular member 416), this step can be accomplished by applying a proximally-directed force on any suitable portion of the intermediate member such that each of the support posts is withdrawn from its respective passageway. Alternatively, if the intermediate member does not include a support post, this step can be accomplished by applying a proximally-directed force on any suitable portion of the intermediate member such that is free of contact with the tubular member.

Alternatively, if the intermediate member has a structural configuration similar to that described below with respect to intermediate member 814, this step can be accomplished by applying a transverse force on the intermediate member relative to the lengthwise axis of the tubular member, a transverse force on the tubular member relative to the lengthwise axis of the intermediate member, or by applying a transverse force on both the intermediate member and the tubular member relative to the lengthwise axis of the tubular member such that the intermediate member is separated from the tubular member.

Step 614 can be accomplished by applying a proximally-directed force (e.g., away from the bodily passage) on the tubular member until it has been withdrawn from the bodily passage such that the distal end of the tubular member is disposed proximal to the bodily passage. Optionally, step 614 can be omitted from method 600. For example, step 614 can be omitted in embodiments in which the tubular member is formed of a biodegradable or bioabsorbable material.

An optional step that can be completed prior to withdrawing the tubular member from the bodily passage comprises suturing the tubular member to tissue that is disposed outside of the bodily passage. This step can be accomplished by passing a suture through a passageway defined by the tubular member and through the tissue that is disposed outside of the bodily passage to secure the tubular member to the tissue and within the bodily passage. In embodiments in which the body of the tubular member defines more than one passageway, an optional step than can be completed prior to withdrawing the tubular member from the bodily passage comprises passing a suture through each passageway, or one or more of the passageways, and through the tissue that is disposed outside of the bodily passage to secure the tubular member to the wall that defines the bodily passage.

A step that can be completed in addition to, or alternative to, the optional steps described above and prior to withdrawing the tubular member from the bodily passage comprises suturing the tubular member to the wall that defines the bodily passage. This step can be accomplished by passing a suture through a passageway defined by the tubular member and through the bodily passage wall to secure the tubular member to the bodily passage wall and within the bodily passage. In embodiments in which the body of the tubular member defines more than one passageway, this step comprises passing a suture through each passageway, or one or more of the passageways, and through the bodily passage wall to secure the tubular member to the bodily passage wall.

An optional step that can be completed prior to withdrawing the tubular member from the bodily passage comprises leaving the tubular member in the bodily passage for an interval of time. Any suitable interval of time is considered suitable, and skilled artisans will be able to select a suitable interval of time to leave a tubular member in a bodily passage according to a particular embodiment based on various considerations, including the treatment intended to be performed. Example intervals of time considered suitable to leave a tubular member within a bodily passage include one or more minutes, one or more hours, one or more days, and any other interval of time considered suitable for a particular application.

Another optional step that can be completed prior to withdrawing the tubular member from the bodily passage comprises passing a medication and/or medical device through the lumen defined by the tubular member and into the bodily passage to perform treatment. Alternatively, a medical device can be passed through a portion of the lumen defined by the tubular member. This step can be accomplished using any suitable medication and/or medical device, and skilled artisans will be able to select a suitable medication and/or medical device to pass through the entirety, or a portion, of a tubular member according to a particular embodiment based on various considerations, including the treatment intended to be performed. Example medical devices considered suitable to pass through the lumen defined by a tubular member include suction catheters, balloon catheters, irrigation catheters, a camera, a light source, and any other medical device considered suitable for a particular application. Another optional step comprises performing treatment with a medical device that has been passed through a portion, or the entirety, of the lumen defined by the tubular member. Another optional step comprises withdrawing the medical device from the lumen defined by the tubular member.

While various steps, alternative steps, and optional steps have been described above with respect to treating a bodily passage, these steps, alternative steps, and optional steps can be included in, accomplished concurrently with, and/or accomplished in the alternative to, the methods, steps, alternative steps, and/or optional steps described below with respect to method of treatment 700.

Figure 8:
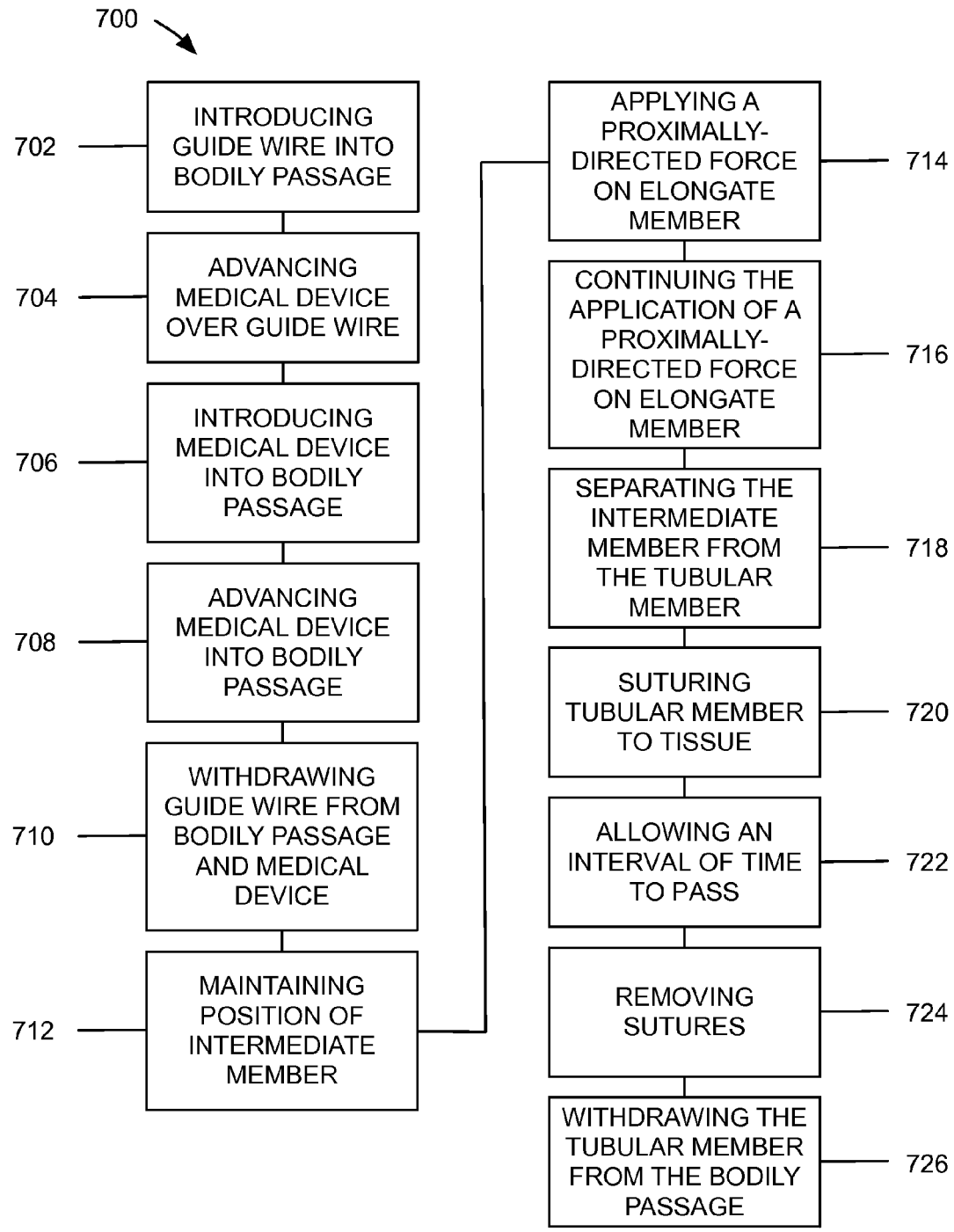
FIG. 8 is a flowchart representation of another method of treatment.

FIG. 8 is a flowchart representation of another method 700 of treating a bodily passage.

A step 702 comprises introducing a guide wire having a guide wire proximal end and a guide wire distal end into a bodily passage such that the guide wire distal end is disposed within the bodily passage. The bodily passage is defined by a bodily passage wall. Another step 704 comprises advancing a medical device having a medical device proximal end and a medical device distal end over the guide wire such that the guide wire is disposed within a lumen defined by an elongate member of the medical device. Another step 706 comprises introducing the medical device into the bodily passage such that the medical device distal end is disposed within the bodily passage. Another step 708 comprises advancing the medical device into the bodily passage until the second outside diameter of the tubular member is disposed within the bodily passage. Another step 710 comprises withdrawing the guide wire from the bodily passage and the medical device. Another step 712 comprises maintaining the position of the intermediate member relative to the tubular member. Another step 714 comprises applying a proximally-directed force on the elongate member while maintaining the position of the intermediate member such that the elongate member is advanced proximally relative to the intermediate member and the tubular member. Another step 716 comprises continuing the application of a proximally-directed force on the elongate member while maintaining the position of the intermediate member until the elongate member is free of the intermediate member and the tubular member. Another step 718 comprises separating the intermediate member from the tubular member. Another step 720 comprises suturing the tubular member to tissue. Another step 722 comprises allowing an interval of time to pass. Another step 724 comprises removing the sutures from the tissue and the tubular member. Another step 726 comprises withdrawing the tubular member from the bodily passage.

Step 702 can be accomplished using any suitable guide wire having any suitable length and structural arrangement. Skilled artisans will be able to select a guide wire to introduce into a bodily passage according to a particular embodiment based on various considerations, including the treatment intended to be performed. Step 702 can be accomplished by applying a distally-directed force (e.g., toward the bodily passage) on any suitable portion of the guide wire such that the guide wire distal end is advanced into the bodily passage.

Step 702 can be accomplished by introducing a guide wire into any suitable bodily passage. Skilled artisans will be able to select a suitable bodily passage to introduce a guide wire according to a particular embodiment based on various considerations, including the treatment intended to be performed. Example bodily passages considered suitable to introduce a guide wire include a salivary duct, a portion of the urinary tract, and any other bodily passage considered suitable for a particular application.

Step 704 can be accomplished using any suitable medical device according to an embodiment, such as the embodiments described and illustrated herein. Skilled artisans will be able to select a suitable medical device to advance over a guide wire according to a particular embodiment based on various considerations, including the treatment intended to be performed. Examples of medical devices considered suitable to advance over a guide wire to complete one or more steps and/or methods described herein include medical devices that include an elongate member that defines a lumen that extends from the proximal end of the elongate member to the distal end of the elongate member (e.g., elongate member 212). Any of the medical devices described and illustrated herein, such as medical device 10, medical device 210, medical device 410, medical device 810, medical devices that include the alternative components described herein (e.g., elongate member 12', intermediate member 14', intermediate member 814', tubular member 1016), are considered suitable and can include an elongate member that defines a lumen that extends from the proximal end of the elongate member to the distal end of the elongate member.

Step 704 can be accomplished by passing the proximal end of the guide wire through a distal opening of the lumen defined by the elongate member (e.g., lumen 324 of elongate member 212) and applying a distally-directed force (e.g., toward the bodily passage) on any suitable portion of the medical device such that the guide wire is passed through the a proximal opening of the lumen and the medical device is disposed on the guide wire.

Step 706 can be accomplished as described above with respect to step 602 and by applying a distally-directed force (e.g., toward the bodily passage) on any suitable portion of the medical device such that the medical device distal end is advanced distally over the guide wire and introduced into the bodily passage.

Step 708 can be accomplished by applying a distally-directed force (e.g., toward the bodily passage) on any suitable portion of the medical device such that the medical device distal end is advanced into the bodily passage, over the guide wire, and the second outside diameter of the tubular member is disposed within the bodily passage. For example, a distally-directed force can be applied to an elongate member of an embodiment, such as elongate member 12, elongate member 12', elongate member 212, elongate member 412, or elongate member 812.

An optional step comprises advancing the medical device into the bodily passage such that the flared proximal portion of the tubular member contacts tissue disposed outside of the bodily passage. This step can be accomplished by placing a distally-directed force on any suitable portion of the medical device until the distal surface of the flared proximal portion contacts the tissue disposed outside of the bodily passage. Alternatively, if the tubular member omits the inclusion of a flared proximal portion, such as tubular member 416, an optional step comprises advancing the medical device into the bodily passage such that the second surface of the tubular member contacts tissue disposed outside of the bodily passage. This step can be accomplished by placing a distally-directed force on any suitable portion of the medical device until the second surface of the tubular member contacts the tissue disposed outside of the bodily passage. Alternatively, if the tubular member defines a constant, or substantially constant diameter along a proximal portion of its length, an optional step comprises advancing the medical device into the bodily passage such that the proximal end of the tubular member is disposed adjacent, or near, an opening of the bodily passage. This step can be accomplished by placing a distally-directed force on any suitable portion of the medical device until the distal surface of second surface of the tubular member contacts the tissue disposed outside of the bodily passage.

Step 710 can be accomplished by applying a proximally-directed force (e.g., away from the bodily passage) on any suitable portion of the guide wire such that the guide wire is withdrawn from the bodily passage and the lumen defined by the elongate member. Optionally, this step can be completed prior to step 720 or step 722.

Step 712 can be accomplished by maintaining the position of the intermediate member relative to the tubular member. This step can be accomplished by applying any suitable force (e.g., distally-directed, proximally-directed, radially-directed) on the intermediate member such that the position of the intermediate member is maintained relative to the tubular member, the tissue disposed outside of the bodily passage, and/or the bodily passage.

Step 714 can be accomplished by applying a proximally-directed force (e.g., away from the bodily passage) on any suitable portion of the elongate member while maintaining the position of the intermediate member relative to the tubular member such that the elongate member is advanced proximally relative to the intermediate member and tubular member and the elongate member is advanced proximally through the lumen defined by the tubular member. For example, step 714 can be accomplished concurrently with step 712. Proximally-directed force can be applied to the proximal portion 30, proximal portion 30', proximal portion 230, proximal portion 430, proximal portion 830, or any other portion of an elongate member considered suitable for a particular application.

Step 716 can be accomplished by continuing the application of a proximally-directed force (e.g., away from the bodily passage) on the elongate member while maintaining the position of the intermediate member relative to the tubular member until the distal end of the shaft is disposed proximal to the proximal end of the intermediate member and the elongate member is free of the intermediate member and the tubular member.

Step 718 can be accomplished by applying a proximally-directed force (e.g., away from the bodily passage) on any suitable portion of the intermediate member (e.g., disc-shaped portion 67, cuboid portion 267, disc-shaped portion 467) such that the support post is withdrawn from the passageway defined by the tubular member. Alternatively, if the intermediate member includes more than one support post and the tubular member defines more than one passageway (e.g., intermediate member 414, tubular member 416), this step can be accomplished by applying a proximally-directed force (e.g., away from the bodily passage) on any suitable portion of the intermediate member such that each of the support posts is withdrawn from its respective passageway. Alternatively, if the intermediate member has a structural configuration similar to that described below with respect to intermediate member 814, this step can be accomplished by applying a transverse force on the intermediate member relative to the lengthwise axis of the tubular member, a transverse force on the tubular member relative to the lengthwise axis of the intermediate member, or by applying a transverse force on both the intermediate member and the tubular member relative to the lengthwise axis of the tubular member such that the intermediate member is separated from the tubular member.

Step 720 can be accomplished by suturing the tubular member to tissue that is disposed outside of the bodily passage. This step can be accomplished by passing one or more sutures through a passageway defined by the tubular member and through the tissue that is disposed outside of the bodily passage to secure the tubular member to the tissue and within the bodily passage. In embodiments in which the body of the tubular member defines more than one passageway, an alternative step than can be completed prior to withdrawing the tubular member from the bodily passage comprises passing one or more sutures through each passageway, or one or more of the passageways, and through the tissue that is disposed outside of the bodily passage to secure the tubular member to the wall that defines the bodily passage.

An optional step that can be completed in addition, or alternative to, step 720 comprises suturing the tubular member to tissue that defines the bodily passage. This step can be accomplished by passing one or more sutures through a passageway defined by the tubular member and through the tissue that defines the bodily passage to secure the tubular member to the tissue and within the bodily passage. In embodiments in which the body of the tubular member defines more than one passageway, this step comprises passing one or more sutures through each passageway, or one or more of the passageways, and through the tissue that defines the bodily passage to secure the tubular member to the wall that defines the bodily passage.

Step 722 can be accomplished by allowing an interval of time to pass before removing the sutures and withdrawing the tubular member from the bodily passage. Any suitable interval of time is considered suitable, and skilled artisans will be able to select a suitable interval of time to leave a tubular member in a bodily passage according to a particular embodiment based on various considerations, including the treatment intended to be performed. Example intervals of time considered suitable to leave a tubular member within a bodily passage include one or more minutes, one or more hours, one or more days, and any other interval of time considered suitable for a particular application.

Step 724 can be accomplished by removing the one or more sutures such that the tubular member can be removed from the bodily passage. Optionally, step 724 can be omitted from method 700. For example, step 724 can be omitted in embodiments in which the one or more sutures are formed of a biodegradable or bioabsorbable material.

Step 726 can be accomplished by applying a proximally-directed force (e.g., away from the bodily passage) on the tubular member until it has been withdrawn from the bodily passage such that the distal end of the tubular member is disposed proximal to the bodily passage. Optionally, step 726 can be omitted from method 700. For example, step 726 can be omitted in embodiments in which the tubular member is formed of a biodegradable or bioabsorbable material.

While various steps, alternative steps, and optional steps have been described above with respect to treating a bodily passage, these steps, alternative steps, and optional steps can be included in, accomplished concurrently with, and/or accomplished in the alternative to, the methods, steps, alternative steps, and/or optional steps described above with respect to method of treatment 600.

FIGS. 9, 10, 11, 12, 13, 14, and 15 illustrate another medical device 810. Medical device 810 is similar to the medical device 10 illustrated in FIGS. 1, 2, and 3 and described above, except as detailed below. Thus, the medical device 810 comprises an elongate member 812, an intermediate member 814, and a tubular member 816.

In this embodiment, the proximal portion 830 has a first outside diameter 837 and a second outside diameter 839 and the body 828 of the elongate member 812 defines a protuberance 930. The first outside diameter 837 of the proximal portion 830 is disposed on the distal end 836 of the proximal portion 830 and the second outside diameter 839 of the proximal portion 830 is disposed on the proximal end 834 of the proximal portion 830. The first outside diameter 837 is greater than the second outside diameter 839. The body 828 of the elongate member 812 defines the first outside diameter 837 along a first portion 838 of the proximal portion 830 and the second outside diameter 839 along a second portion 840 of the proximal portion 830. The first portion 838 extends from the distal end 836 toward the proximal end 834 to the second portion 840 and has a length that is less than the length 835 of the proximal portion 830. The second portion 840 extends from the first portion 838 to the proximal end 834 of the proximal portion 830 and has a length that is greater than the length 835 of the proximal portion 830. However, other structural arrangements are considered suitable, such as a first portion that has a length that is greater than, equal to, or substantially equal to, the length of a second portion.

The protuberance 930 is defined between the proximal end 844 of the shaft 832 and the distal end 846 of the shaft 832. The protuberance 930 extends outward and away from the shaft 832 and has an outside diameter 931 and a thickness 932. The outside diameter 931 of the protuberance 930 is greater than the first outside diameter 847 of the shaft 832 that extends from the protuberance 930 toward the distal end 846 of the shaft 832. The thickness 932 of the protuberance 930 extends from the proximal end of the protuberance 930 to the distal end of the protuberance 930 and can be any suitable thickness capable of releasably attaching the intermediate member 814 to the elongate member 812, as described in more detail herein. The portion of the shaft 832 disposed between the proximal portion 830 and the protuberance 930 has an outside diameter that is less than the outside diameter 931 of the protuberance 930. In the illustrated embodiment, the portion of the shaft 832 disposed between the proximal portion 830 and the protuberance 930 has an outside diameter that is greater than the first outside diameter 847 of the shaft 832 disposed distal to the protuberance 930. However, alternative embodiments can include a portion of the shaft that is disposed between the proximal portion 830 and the protuberance 930 that has an outside diameter that is equal to, substantially equal to, or less than the first outside diameter 847 of the shaft 832 that is distal to the protuberance 930. While the protuberance 930 is described as defined by the body 828 of the elongate member 812, a protuberance can alternatively be a separate component attached to the shaft of an elongate member using any suitable technique or method of attachment, such as welding, or by using adhesives.

In the illustrated embodiment, the body 856 of the intermediate member 814 defines a first opening 858, a second opening 860, a lumen 862, an edge 940, a notch 942, a slot 944, and recess 946. The first opening 858 is disposed on the proximal end 852 and the second opening 860 is defined within the slot 944 (e.g., between the first surface 864 and the second surface 866) such that the second opening 860 is in communication with slot 944. The lumen 862 extends from the first opening 858 to the second opening 860 thereby extending from the proximal end 852 of the intermediate member 814 to the slot 944.

The edge 940 of the intermediate member 814 extends from the first surface 864 to the second surface 866. The notch 942 is defined on the edge 940, interrupts the surface of the edge 940, and is sized and configured to receive a portion of the tubular member 816. The notch 942 is in communication with the first opening 858, second opening 860, and the lumen 862 via slot 944, as described in more detail herein.

The slot 944 is cooperatively defined by the edge 940 and the second surface 866 and extends from the second surface 866 into the intermediate member body 856. The slot 944 extends from the notch 942 defined on the edge 940 to a slot end 948 and from the second surface 866 and into the body 856 of the intermediate member 814. The second opening 860 is disposed between the notch 942 and the slot end 948 such that the slot 944 is in communication with the lumen 862 defined by the intermediate member 814. The slot 944 has a first portion 950 and a second portion 952 and is sized and configured to receive a portion of the tubular member 816 (e.g., flared proximal portion 888). Alternatively, a slot can be sized and configured to receive any suitable tubular member, or portion of a tubular member, such as tubular member 16, tubular member 216, tubular member 416, tubular member 1016, and any other tubular member considered suitable to include in a medical device.

The first portion 950 has a first width 954, a first depth 956, a first height 958, and an end 960. The first width 954 is defined on the second surface 866 and is less than the first outside diameter 887 of the tubular member 816, greater than the second outside diameter 889 of the tubular member 816, and less than the diameter of the second opening 860. However, alternative embodiments can include a first portion that has a width that is greater than the diameter of the second opening and/or less than the second outside diameter of the tubular member such that an interference fit between the intermediate member and the tubular member can be achieved. The first depth 956 extends from the second surface 866 and into the body 856 of the intermediate member 814 toward the first surface 864 and is less than the second depth 964, as described herein. However, alternative embodiments can include a slot that has a first depth that is greater than, equal to, or substantially equal to, the second depth. The first height 958 extends from the edge 940 to the end 960 of the first portion 950 along a portion of the diameter of the intermediate member 814.

The second portion 952 has a second width 962, a second depth 964, a second height 966, and an end 968. The second width 962 is greater than the first width 954 and is disposed between the proximal end 852 and the distal end 854 of the intermediate member 814. Thus, the slot 944 defines a shoulder 970 between the proximal end 852 and the distal end 854 of the intermediate member 814. The second width 962 is greater than the first outside diameter 887 of the tubular member 816. However, alternative embodiments can include a second inside diameter that is less than, equal to, or substantially equal to, the first outside diameter of a tubular member. The second depth 964 extends from the first portion 950 of the slot 944 into the body 856 of the intermediate member 814 and away from the second surface 866 (e.g., toward the first surface 864). The second depth 964 is sized and configured to receive the third portion 896 (e.g., flared proximal portion 888) of the tubular member 816 such that the tubular member 816 can be releasably attached within the slot 944. In the embodiment illustrated, the second depth 964 has a length that is equal to the length of the third portion 896 (e.g., flared proximal portion 888) of the tubular member 816. However, alternative embodiments can include a second depth has a length that is substantially equal to, greater than, or less than, the length of the third portion of the tubular member.

The second height 966 extends from the edge 940 to the end 968 of the second portion 952 and is greater than the first height 958. In the embodiment illustrated, the end 960 of the first portion 950 is disposed a first distance from the center of the intermediate member 814 and the end 968 of the second portion 952 is disposed a second distance from the center of the intermediate member 814. The second distance is greater than the first distance. The end 968 of the second portion 952 is positioned such that when the tubular member 816 is disposed within the slot 944, as shown in FIG. 15, and contacts, or is disposed near the end 968 of the second portion 952, the lumen 862 defined by the intermediate member 814 is aligned with the lumen 886 defined by the tubular member 816 such that they are coaxial and/or in communication with one another.

In the embodiment illustrated, the end 960 of the first portion 950 is configured such that it corresponds to the structural arrangement of the exterior surface of the tubular member 816 along the fourth portion 900. In addition, the end 968 of the second portion 952 is configured such that it corresponds to the structure of the proximal end 876 of the tubular member 816. Thus, the end 960 of the first portion 950 and the end 968 of the second portion 952 are curved. However, alternative embodiments can include an intermediate member that defines a slot that has any suitable configuration, such as those that correspond to the configuration of the proximal end of a tubular member. Alternatively, the end of the first portion and/or second portion of a slot can be configured such that they do not correspond to the structure of a tubular member.

The recess 946 is defined between the proximal end (e.g., first opening 858) and the distal end of the lumen 862 (e.g., second opening 860) within the lumen 862 and has an inside diameter that is greater than the inside diameter of the lumen 862. The recess 946 extends along a first portion 855 of the intermediate member 814 and is sized and configured to receive the protuberance 930. The diameter of the recess 946 is equal to the outside diameter 931 of the protuberance 930 and the first portion 855 of the intermediate member 814 has a length that is equal to the thickness 932 of the protuberance 930. This configuration provides a snap fit configuration between the elongate member 812 and the intermediate member 814 when the two components are releasably attached to one another. However, alternative embodiments could include a recess that has a diameter that is greater than, substantially equal to, or less than the outside diameter of a protuberance and/or a recess that extends along a portion of the intermediate member that is greater than, substantially equal to, or less than the thickness of the protuberance.

In use, the shaft 832 of the elongate member 812 is passed through lumen 862 such that the protuberance 930 is partially disposed within the recess 946. Depending on the structural configuration of the recess defined by an intermediate member, alternative embodiments can include a protuberance that is entirely disposed within a recess defined by an intermediate member when the two components are releasably attached to one another. In the embodiment illustrated, the intermediate member 814 is formed of a material that is relatively more flexible than the material that forms elongate member 812 such that first opening 858 can expand when protuberance 930 is advanced distally through the lumen 862 and return to its original configuration, or a configuration that is substantially similar to its original configuration, after the protuberance 930 is disposed within the recess 946. Alternatively, a portion (e.g., protuberance), or the entirety, of the shaft can be formed of a material that is relatively more flexible than the material that forms the intermediate member such that the protuberance can compress and allow the intermediate member to be passed over the protuberance until the protuberance is disposed within the recess defined by the intermediate member.

While an interlocking structure has been illustrated between the elongate member 812 and the intermediate member 814, any suitable locking structure can be included on an elongate member and/or an intermediate member to provide releasable attachment between the elongate member and the intermediate member. Skilled artisans will be able to select a suitable locking structure to include on an elongate member and/or intermediate member according to a particular embodiment based on various considerations, including the material(s) that forms the elongate member and the intermediate member. Example locking structures considered suitable include interlocking structures, structures that provide a friction fit between the elongate member and the intermediate member (e.g., the shaft of the elongate member has an outside diameter that is greater than a portion of the intermediate member lumen such that a friction fit can be achieved), mechanical fasteners, morse taper configurations, and any other structure considered suitable for a particular embodiment.

Figure 19:
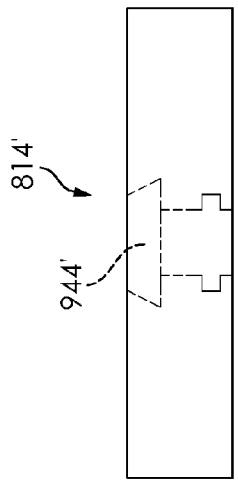
FIG. 19 is a bottom view of another alternative intermediate member.

While the slot 944 has been illustrated as having a particular structural arrangement, a slot defined by an intermediate member can have any suitable structural arrangement capable of releasably attaching a tubular member to the intermediate member. Skilled artisans will be able to select a suitable structural arrangement for a slot according to a particular embodiment based on various considerations, including the structural arrangement of the proximal end of a tubular member and/or the material(s) that forms a tubular member. For example, a slot can be tapered such that it corresponds to the structural arrangement of an embodiment of the proximal end of a tubular member. FIG. 19 illustrates an intermediate member 814' similar to intermediate member 814 except intermediate member 814' defines a slot 944' that has a tapered configuration that corresponds with the structural arrangement of an embodiment of a tubular member (e.g., tubular member 16, tubular member 216, tubular member 816). Alternatively, a slot can extend from an opening defined on a surface of an intermediate member (e.g., second surface of an intermediate member) to a slot end. In these embodiments, the proximal end of the tubular member can be advanced through the opening defined on the surface of the intermediate member and toward the slot end to align the lumen defined by the tubular member with the lumen defined by the intermediate member such that they are coaxial an/or in communication with one another.

In the illustrated embodiment, the first opening 882 of the tubular member 816 has a diameter that is equal to the diameter of the lumen 862 defined by the intermediate member 814. However, the first opening of a tubular member can have any suitable diameter, such as a diameter that is greater than, less than, or equal to, the diameter of the lumen defined by an intermediate member.

The intermediate member 814 and the tubular member 816 have a first configuration and a second configuration. In the first configuration, the tubular member 816 is free of the intermediate member 814, as shown in FIG. 14. In the second configuration, the tubular member 816 is partially disposed within the slot 944 defined by the intermediate member 814 such that the tubular member 816 is releasably attached to the intermediate member 814, as shown in FIGS. 9 and 15. To assemble the medical device 810, the proximal end 876 of the tubular member 816 is positioned near the notch 942 defined on the edge 940 of the intermediate member 814, as shown in FIG. 14, and is advanced into slot 944, as shown in FIG. 15. The tubular member 816 is advanced into the slot 944 by applying a transverse force on the intermediate member 814 relative to the lengthwise axis of the tubular member 816, a transverse force on the tubular member 816 relative to the lengthwise axis of the intermediate member 814, or by applying a transverse force on both the intermediate member 814 and the tubular member 816 relative to the lengthwise axis of the tubular member 816. The transverse force(s) is applied until the lumen 862 defined by the intermediate member 814 is in communication with the lumen 886 defined by the tubular member 816 (e.g., lumen 862 defined by the intermediate member 814 is aligned, or coaxial, with the lumen 886 defined by the tubular member 816). Thus, when assembled, the tubular member 816 is partially disposed within the slot 944 defined by the intermediate member 814. Subsequently, the distal end 826 of the elongate member 812 is advanced through the lumen 862 defined by the intermediate member 814 and the lumen 886 defined by the tubular member 816 until the protuberance 930 is disposed within the recess 946 defined by the intermediate member 814 and the distal end 836 of the proximal portion 830 contacts the first surface 864 of the intermediate member 814.

When the medical device 810 is fully assembled, as illustrated in FIG. 9, the intermediate member 814 is releasably attached to the tubular member 812 and is disposed on the shaft 832 such that a portion of the intermediate member 814 is disposed between the distal end 836 of the proximal portion 830 and the proximal end 876 of tubular member 816. Thus, a portion of the intermediate member 814 is disposed between the proximal portion 830 and the tubular member 816.

Figure 17:
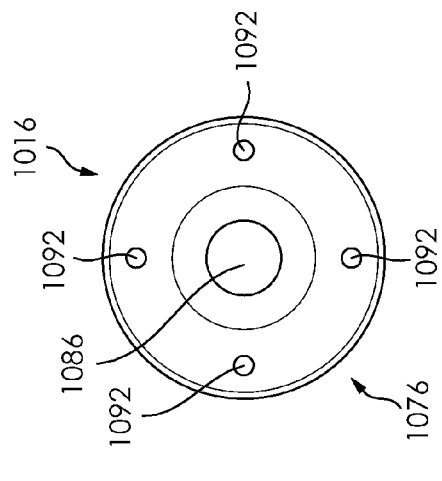
FIG. 17 is an end view of the proximal end of the tubular member illustrated in FIG. 16.
Figure 16:
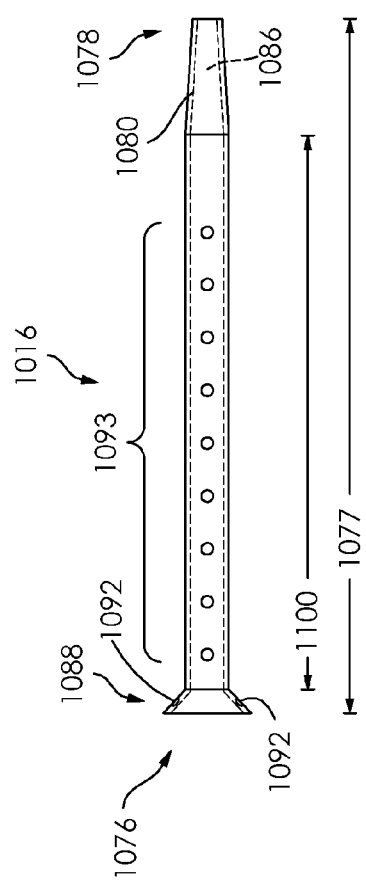
FIG. 16 is a side view of an alternative tubular member.
Figure 18:
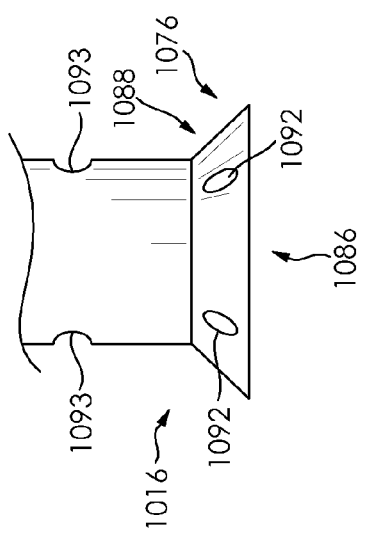
FIG. 18 is a partial side view of the proximal end of the tubular member illustrated in FIG. 16.

FIGS. 16, 17, and 18 illustrate an alternative tubular member 1016. Tubular member 1016 is similar to the tubular member 16 illustrated in FIGS. 1, 2, and 3 and described above, except as detailed below. Thus, the tubular member 1016 comprises a proximal end 1076, a distal end 1078, and a body 1080.

In the embodiment illustrated, the body 1080 of the tubular member 1016 defines a first set of passageways 1092 on the flared proximal portion 1088 and a second set of passageways 1093 on the fourth portion 1100 of the tubular member 1016. Each passageway in the first set of passageways 1092 is defined on an axis that is disposed parallel to the lengthwise axis of the tubular member 1016 and provides access to the lumen 1086 defined by the tubular member 1016. However, alternative embodiments can include one or more passageways defined on the flared proximal portion 1088 that are disposed on an axis that is not parallel to the lengthwise axis of the tubular member 1016.

A first portion of the second set of passageways 1093 is disposed on a first side of the fourth portion 1100 of the tubular member 1016 and a second portion of the second set of passageways 1093 is disposed on a second side of the fourth portion 1100 of the tubular member 1016. In the embodiment illustrated, the first portion of the second set of passageways 1093 is opposably positioned from the second portion of the second set of passageways 1093 relative to the lengthwise axis of the tubular member 1016. However, alternative embodiments can include a first portion of a set of passageways that are positioned at any suitable location on a tubular member relative to a second portion of the set of passageways (e.g., first portion is not opposably positioned from the second portion).

Each passageway in the second set of passageways 1093 is defined on an axis that is disposed orthogonal to the lengthwise axis of the tubular member 1016 and provides access to the lumen 1086 defined by the tubular member 1016. However, alternative embodiments can include one or more passageways defined on the fourth portion 1100 of the tubular member 1016 that are disposed on an axis that is not orthogonal to the lengthwise axis of the tubular member 1016.

Each passageway of the first set of passageways 1092 and second set of passageways 1093 has a diameter that is sized and configured to receive a thread, the same thread a plurality of times, or a plurality of threads, such that the tubular member 1016 can be sutured to the tissue disposed outside of the bodily passage and/or the bodily passage wall. In addition, each passageway of the first set of passageways 1092 and second set of passageways 1093 has a diameter that is sized and configured to allow a fluid, such as saliva, to pass through the passageway and enter the lumen 1086 such that the fluid can pass through the device and exit through the opening defined on the proximal end (e.g., if the distal opening were to become occluded) and/or the opening on the distal end of the tubular member (e.g., if the proximal opening were to become occluded). For example, if the distal end of the tubular member 1016 were to become occluded during use, or was occluded, saliva can enter the lumen 1086 through one or more of the passageways of the first set of passageways 1092 and/or second set of passageways 1093 and exit the tubular member 1016 through the proximal opening. A tubular member can be configured such that it has an outside diameter that decreases from the proximal end of the tubular member to the distal end of the tubular member (e.g., a first outside diameter at the proximal end and a second outside diameter at the distal end that is less than the first outside diameter) to allow for a fluid, such as saliva, to pass through a lumen defined by the tubular member. Alternatively, or in combination with a decreasing outside diameter, the tubular member can define one or more steps, or shoulders, along its length that reduces the outside diameter of the tubular member from a portion located proximal to the step, or shoulder, to a portion located distal of the step, or shoulder.

While a first set of passageways 1092 has been illustrated as defined on the flared proximal portion 1088 and a second set of passageways 1093 has been illustrated as defined on the fourth portion 1100 of the tubular member 1016, any suitable number of passageways can be defined on any suitable portion of a tubular member. Skilled artisans will be able to select a suitable number of passageways to define on a tubular member and a suitable location to position each passageway according to a particular embodiment based on various considerations, including the number of support posts defined by an intermediate member included in a medical device of which the tubular member is a component and/or the desired location to suture a tubular member to the tissue disposed outside of the bodily passage and/or the bodily passage wall. Example number of passageways considered suitable to include on a tubular member include one, at least one, two, a plurality, three, four, five, six, seven, and any other number considered suitable for a particular application. For example, a suitable number of passageways to include in a first set of passageways defined on a tubular member includes two, a plurality, three, four, and any other number of passageways considered suitable for a particular embodiment. For example, a suitable number of passageways to include in a second set of passageways defined on a tubular member includes two, a plurality, three, four, and any other number of passageways considered suitable for a particular embodiment. Alternatively, a single passageway can be included on the flared proximal portion of a tubular member and/or a single passageway can be included on the fourth portion of the tubular member. Example locations considered suitable to define a passageway on a tubular member include on the flared proximal portion of a tubular member, between the proximal end and the distal end of a tubular member, on the tapered distal portion of a tubular member, and any other location considered suitable for a particular embodiment.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A medical device for the treatment of a bodily passage, said medical device comprising:
an elongate member having a proximal portion and a shaft extending distally from the proximal portion, the proximal portion having a first proximal end, a first distal end, and a first outside diameter, the shaft having a second proximal end attached to the first distal end of the proximal portion, a second distal end, and a second outside diameter that is less than the first outside diameter;
an intermediate member releasably attached to the elongate member and disposed on the shaft, the intermediate member having a third proximal end, a third distal end, a first surface, a second surface, an intermediate member body, and a third outside diameter that is greater than the first outside diameter of the proximal portion of the elongate member, the intermediate member body defining a first intermediate member opening, a second intermediate member opening, an intermediate member lumen, an edge, and a slot, the first intermediate member opening defined on the first surface of the intermediate member, the second intermediate member opening defined between the first surface and the second surface and in communication with the slot, the intermediate member lumen extending from the first intermediate member opening to the second intermediate member opening, the intermediate member lumen having a first inside diameter that is less than the first outside diameter of the proximal portion of the elongate member, the edge extending from the first surface to the second surface of the intermediate member, the slot cooperatively defined by the edge and the second surface and extending from the second surface into the intermediate member body; and a tubular member partially disposed within the slot defined by the intermediate member such that the tubular member is releasably attached to the intermediate member, the tubular member disposed on the shaft of the elongate member and having a fourth proximal end, a fourth distal end, and a tubular member body defining a first tubular member opening on the fourth proximal end, a second tubular member opening on the fourth distal end, and a tubular member lumen extending from the first tubular member opening to the second tubular member opening.

2. The medical device of claim 1, wherein the slot has a first portion and a second portion, the first portion extending from the second surface toward the first surface of the intermediate member and having a first width, the second portion extending from the first portion toward the first surface of the intermediate member and having a second width that is greater than the first width.

3. The medical device of claim 2, wherein the tubular member body defines a proximal portion extending from the fourth proximal end toward the fourth distal end and a distal portion extending from the fourth distal end toward the fourth proximal end, the proximal portion of the tubular member having a fourth outside diameter that is greater than the first width of the slot, and the distal portion of the tubular member having a fifth outside diameter that is less than the fourth outside diameter; and wherein the proximal portion of the tubular member is disposed within the slot defined by the intermediate member.

4. The medical device of claim 3, wherein the proximal portion of the tubular member is frustoconical and tapers from the fourth proximal end toward the fourth distal end.

5. The medical device of claim 3, wherein the tubular member body defines a passageway on the proximal portion of the tubular member, the passageway extending through the tubular member body and providing access to the tubular member lumen.

6. The medical device of claim 3, wherein the tubular member body defines a passageway between the proximal portion of the tubular member and the fourth distal end, the passageway extending through the tubular member body and providing access to the tubular member lumen.

7. The medical device of claim 1, wherein the intermediate member lumen is in communication with the tubular member lumen.

8. The medical device of claim 1, wherein the intermediate member body defines a recess between the first intermediate member opening and the second intermediate member opening within the intermediate member lumen, the recess having a second inside diameter that is greater than the first inside diameter of the intermediate member lumen.

9. The medical device of claim 8, wherein the shaft has a protuberance disposed between the second proximal end and the second distal end, the protuberance having a fourth outside diameter that is greater than the second outside diameter of the shaft; and wherein the protuberance is disposed within the recess defined by the intermediate member.

10. The medical device of claim 1, wherein the second distal end is tapered;

wherein the fourth distal end is tapered; and wherein the fourth distal end of the tubular member is disposed between the second proximal end and the second distal end of the shaft.

11. The medical device of claim 1, wherein the shaft has a first length extending from the second proximal end to the second distal end;

wherein the tubular member has a second length extending from the fourth proximal end to the fourth distal end; and wherein the first length of the shaft is greater than the second length of the tubular member.

12. A medical device for the treatment of a bodily passage, said medical device comprising:

an elongate member having a proximal portion and a shaft extending distally from the proximal portion, the proximal portion having a first proximal end, a first distal end, and a first outside diameter, the shaft having a second proximal end attached to the first distal end of the proximal portion, a second distal end, and a second outside diameter that is less than the first outside diameter;

an intermediate member releasably attached to the elongate member and disposed on the shaft, the intermediate member having a third proximal end, a third distal end, a first surface, a second surface, an intermediate member body, and a third outside diameter that is greater than the first outside diameter of the proximal portion of the elongate member, the intermediate member body defining a first intermediate member opening, a second intermediate member opening, an intermediate member lumen, an edge, and a slot, the first intermediate member opening defined on the first surface of the intermediate member, the second intermediate member opening defined between the first surface and the second surface and in communication with the slot, the intermediate member lumen extending from the first intermediate member opening to the second intermediate member opening, the intermediate member lumen having a first inside diameter that is less than the first outside diameter of the proximal portion of the elongate member, the edge extending from the first surface to the second surface of the intermediate member, the slot cooperatively defined by the edge and the second surface and extending from the second surface into the intermediate member body, the slot having a first portion and a second portion, the first portion extending from the second surface toward the first surface and having a first width, the second portion extending from the first portion toward the first surface and having a second width that is greater than the first width; and a tubular member partially disposed within the slot defined by the intermediate member such that the tubular member is releasably attached to the intermediate member, the tubular member disposed on the shaft of the elongate member and having a fourth proximal end, a fourth distal end, and a tubular member body defining a first tubular member opening on the fourth proximal end, a second tubular member opening on the fourth distal end, a tubular member lumen extending from the first tubular member opening to the second tubular member opening, a proximal portion extending from the fourth proximal end toward the fourth distal end, and a distal portion extending from the fourth distal end toward the fourth proximal end, the proximal portion of the tubular member having a fourth outside diameter that is greater than the first width of the slot, the distal portion of the tubular member having a fifth outside diameter that is less than the fourth outside diameter, the proximal portion of the tubular member disposed within the slot defined by the intermediate member;

wherein the intermediate member lumen is in communication with the tubular member lumen.

13. The medical device of claim 12, wherein the proximal portion of the tubular member is frustoconical and tapers from the fourth proximal end toward the fourth distal end.

14. The medical device of claim 12, wherein the tubular member body defines a passageway on the proximal portion of the tubular member, the passageway extending through the tubular member body and providing access to the tubular member lumen.

15. The medical device of claim 12, wherein the tubular member body defines a passageway between the proximal portion of the tubular member and the fourth distal end, the passageway extending through the tubular member body and providing access to the tubular member lumen.

16. The medical device of claim 12, wherein the intermediate member body defines a recess between the first intermediate member opening and the second intermediate member opening within the intermediate member lumen, the recess having a second inside diameter that is greater than the first inside diameter of the intermediate member lumen.

17. The medical device of claim 16, wherein the shaft has a protuberance disposed between the second proximal end and the second distal end, the protuberance having a sixth outside diameter that is greater than the second outside diameter of the shaft; and wherein the protuberance is disposed within the recess defined by the intermediate member.

18. The medical device of claim 12, wherein the second distal end is tapered;

wherein the fourth distal end is tapered; and wherein the fourth distal end of the tubular member is disposed between the second proximal end and the second distal end of the shaft.

19. The medical device of claim 12, wherein the shaft has a first length extending from the second proximal end to the second distal end;

wherein the tubular member has a second length extending from the fourth proximal end to the fourth distal end; and wherein the first length of the shaft is greater than the second length of the tubular member.

20. A medical device for the treatment of a bodily passage, said medical device comprising:

an elongate member having a proximal portion and a shaft extending distally from the proximal portion, the proximal portion having a first proximal end, a first distal end, and a first outside diameter, the shaft having a second proximal end attached to the first distal end of the proximal portion, a tapered second distal end, a second outside diameter that is less than the first outside diameter, and a protuberance disposed between the second proximal end and the second distal end, the protuberance having a third outside diameter that is greater than the second outside diameter of the shaft;

an intermediate member releasably attached to the elongate member and disposed on the shaft, the intermediate member having a third proximal end, a third distal end, a first surface, a second surface, an intermediate member body, and a fourth outside diameter that is greater than the first outside diameter of the proximal portion of the elongate member, the intermediate member body defining a first intermediate member opening, a second intermediate member opening, an intermediate member lumen, an edge, a slot, and a recess, the first intermediate member opening defined on the first surface of the intermediate member, the second intermediate member opening defined between the first surface and the second surface and in communication with the slot, the intermediate member lumen extending from the first intermediate member opening to the second intermediate member opening, the intermediate member lumen having a first inside diameter that is less than the first outside diameter of the proximal portion of the elongate member, the edge extending from the first surface to the second surface of the intermediate member, the slot cooperatively defined by the edge and the second surface and extending from the second surface into the intermediate member body, the slot having a first portion and a second portion, the first portion extending from the second surface toward the first surface and having a first width, the second portion extending from the first portion toward the first surface and having a second width that is greater than the first width, the recess defined between the first intermediate member opening and the second intermediate member opening within the intermediate member lumen and having a second inside diameter that is greater than the first inside diameter of the intermediate member lumen; and a tubular member partially disposed within the slot defined by the intermediate member such that the tubular member is releasably attached to the intermediate member, the tubular member disposed on the shaft of the elongate member and having a fourth proximal end, a tapered fourth distal end, and a tubular member body defining a first tubular member opening on the fourth proximal end, a second tubular member opening on the fourth distal end, a tubular member lumen extending from the first tubular member opening to the second tubular member opening, a frustoconical proximal portion extending from the fourth proximal end and tapering toward the fourth distal end, and a distal portion extending from the fourth distal end toward the fourth proximal end, the frustoconical proximal portion of the tubular member having a fifth outside diameter that is greater than the first width of the slot, the distal portion of the tubular member having a sixth outside diameter that is less than the fifth outside diameter, the frustoconical proximal portion of the tubular member disposed within the slot defined by the intermediate member;

wherein the intermediate member lumen is in communication with the tubular member lumen;

wherein the protuberance is disposed within the recess defined by the intermediate member; and wherein the fourth distal end of the tubular member is disposed between the second proximal end and the second distal end of the shaft.

* * * * *